United States Patent [19]

Curiel

[11] Patent Number: 5,871,727
[45] Date of Patent: Feb. 16, 1999

[54] TARGETED ADENOVIRUS VECTORS

[75] Inventor: David T. Curiel, Birmingham, Ala.

[73] Assignee: UAB Research Foundation, Birmingham, Ala.

[21] Appl. No.: 761,242

[22] Filed: Dec. 6, 1996

Related U.S. Application Data

[60] Provisional application No. 60/008,375 Dec. 8, 1995 and provisional application No. 60/020,163 Jun. 20, 1995.

[51] Int. Cl.⁶ ............................. C12N 5/00; C12N 15/00; A61K 48/00
[52] U.S. Cl. ........................ 424/93.2; 514/44; 435/172.3; 435/320.1
[58] Field of Search ................................ 435/69.1, 172.3, 435/320.1; 424/93.2; 536/23.1; 517/44

[56] References Cited

U.S. PATENT DOCUMENTS 5,543,328   8/1996   McClelland et al. ................ 435/320.1

OTHER PUBLICATIONS

Marshall, E (1995) Science 269: 1050–1055.
Miller et al (1995) FASEB J. 9 : 190–199.

*Primary Examiner*—Bruce R. Campell
*Attorney, Agent, or Firm*—Benjamin Aaron Adler

[57] ABSTRACT

The present invention provides means to modify the tropism of recombinant adenoviral vectors using genetic methods to alter the adenoviral fiber cell-binding protein. The present invention generates an adenovirus with modified fiber gene using a two-plasmid rescue system for derivation of adenoviral fiber recombinants.

10 Claims, 22 Drawing Sheets

TARGETED ADENOVIRUS VECTORS

FEDERAL FUNDING LEGEND

This work was supported by grants from the National Institutes of Health (R01 5025505) and the U.S. Army—DAMD (17-94-J-4398). The Federal Government has certain rights in this invention.

BACKGROUND OF THE INVENTION

This application claims the benefit of U.S. Provisional Application No. 60/008,375 filed Dec. 8, 1995 and U.S. Provisional Application No. 60/020,163 filed Jun. 20, 1996.

1. Field of the Invention

The present invention relates generally to the fields of molecular biology and gene theapy. More specifically, the present invention relates to the production of recombinant adenoviral vectors with modified fibers for the purpose of cell-specific targeting.

2. Description of the Related Art

Recombinant adenoviruses have demonstrated great utility in the context of a variety of strategies to accomplish gene therapy (1-3). One of the principal features of recombinant adenoviruses resulting in their frequent use relates to the unique ability of these vectors to accomplish direct in vivo gene delivery. In this regard, recombinant adenoviral vectors have been shown to be capable of efficient gene transfer to parenchymal cells of various organs including the lung, the brain, the pancreas, the gall bladder, the liver, and others (4-12). This has allowed the utilization of recombinant adenoviral vectors as an approach to treat inherited genetic diseases, such as cystic fibrosis, whereby the delivered vector may be contained within the target organ (4-13). In addition, the ability of the adenoviral vector to accomplish in situ tumor transduction has allowed the development of a variety of anti-cancer gene therapy approaches for loco-regional disease (14-18, 45). Again, these approaches have been directed towards non-disseminated disease, whereby vector containment favors tumor cell-specific transduction.

Despite the versatility of the adenoviral vector in these contexts, the full utility of the recombinant virions for in vivo gene transfer applications is not currently exploitable. This is because the promiscuous tropism of the virus allows widespread, unrestricted tissue transduction after systemic in vivo vector delivery (19, 20). Thus, approaches based upon vascular vector delivery to specific organ sites would be undermined by ectopic, non-targeted cellular transduction. This biologic feature of the virion has thus limited gene therapy approaches to the aforementioned loco-regional or compartment disease models whereby anatomic containment favors some level of selective target cell transduction.
Adenoviruses as vectors for gene therapy The approach of direct intramuscular injection, whether of naked DNA or of viral vectors, as a method for in vivo gene transfer in various genetic diseases suffers from practical limitations. The injection of the large mass of skeletal tissue would be impractical in a clinical context. However, the problems associated with Intramuscular injection could be avoided by the targeted delivery to muscle cells of an intravenously administered vector. Adenoviral vectors can accomplish in vivo gene delivery to a variety of organs after intravenous injection. In these instances, gene transfer frequencies have been sufficiently high to correct inherited metabolic abnormalities in various murine models. Thus, adenoviral vectors fulfill two requirements of an intravenously administered vector for gene therapy: systemic stability and the ability to accomplish long-term gene expression following high efficiency transduction of muscle cells. However, adenoviruses suffer from the disadvantage that the widespread distribution of the adenovirus cellular receptor precludes the targeting of specific cell types. This lack of tropism of adenoviral vectors would result in a decrease in the efficiency of transduction, as the number of virus particles available for delivery to the target cells would be decreased by sequestration by nontarget cells. Furthermore, this would allow ectopic expression of the delivered gene, with unknown and possibly deleterious consequences. Therefore a means must be developed to redirect the tropism of the adenovirus vector specifically to target cells to permit gene delivery uniquely to organs affected.

Another recognized problem with the use of existing adenovirus vectors deleted only in the E1 region of the genome is that the low-level expression of late adenovirus gene products triggers an immune response in the host. This is manifested as an inflammatory immune attack on the transduced cells which leads to transient expression of the transgene and precludes repeated gene transfer with the same vector. A further problem associated with the current generation of adenovirus vectors is that the insert capacity is presently limited to about 7.5 kb, whereas many genes cDNA's are much greater in length.

A strategy to overcome this limitation would be the modification of the cell binding domains of the adenovirus to allow interaction with cellular receptors in a specific manner. Adenovirus interacts with eucaryotic cells by virtue of specific receptor recognition by domains in the knob portion of the fiber protein (21-23) which protrude from each of the twelve vertices of the icosahedral capsid.

The prior art is deficient in the lack of effective means to produce recombinant adenoviral vectors with modified fibers for purposes of cell-specific targeting. The present invention fulfills this longstanding need and desire in the art.

SUMMARY OF THE INVENTION

As a further step towards the development of a tropism-modified virus, the present invention discloses a novel genetic method to introduce modified fiber genes into adenoviral particles. The described methods provide a rapid and facile means to produce recombinant adenoviral vectors with modified fibers for purposes of cell-specific targeting. To expand the utility of recombinant adenoviruses for gene therapy applications, methods to alter native vector tropism to achieve cell-specific transduction would be beneficial. To this end, genetic methods are developed to alter the cell recognition domain of the fiber binding protein based upon the generation of fiber-ligand fusions. To incorporate these modified fiber proteins into mature virions, a system has been developed based upon homologous DNA recombination. In this strategy, a fiber-deleted, propagation-defective "fiber rescue" plasmid was designed for recombination with a shuttle vector encoding a variant fiber gene. Incorporation of a luciferase reporter gene into the rescue plasmid provided an additional means of monitoring the viability of progeny viruses. Recombination between the rescue and shuttle plasmids allows rectification of the defect in the rescue plasmid resulting in the derivation of recombinant virus containing the variant fiber gene contained by the shuttle plasmid.

To establish this method, a recombinant adenovirus was constructed containing a fiber with a silent mutation by co-transfection of 293 cells with the fiber rescue plasmid and shuttle plasmid encoding the fiber variant. Thus, this two plasmid system allows for the generation of adenoviral vectors containing variant fiber genes. This method provides a rapid and facile means of generating tropism-modified recombinant adenoviruses with fiber-ligand fusions for purposes of cell-specific targeting.

In one embodiment of the present invention, there is provided a modified adenoviral vector containing fiber gene variants.

The present invention also described the development of a tropism-modified virus and a novel genetic method to introduce modified fiber genes into adenoviral particles. In addition, that incorporation of a chimeric fiber can alter the tropism profile of the derived virus is shown. This method provides a rapid and facile means to produce recombinant adenoviral vectors with modified fibers and the derivation of additional fiber modifications for purposes of cell-specific targeting via tropism-modified adenoviral vectors.

The present invention also describes a method based upon homologous DNA recombination between two plasmids. A fiber-deleted, propagation-defective rescue plasmid has been designed for recombination with a shuttle plasmid encoding a variant fiber gene. Recombination between the two plasmids results in the derivation of recombinant viruses containing the variant fiber gene. A recombinant adenovirus containing a fiber gene with a silent mutation was constructed. In addition, an adenoviral vector containing chimeric fibers composed of the tail and shaft domains of adenovirus serotype 5 and the knob domain of serotype 3 was generated. This modification was shown to alter the receptor recognition profile of the virus containing the fiber chimera. Thus, this two plasmid system allows for the generation of adenoviral vectors containing variant fibers. This method provides a rapid and facile means of generating fiber-modified recombinant adenoviruses. In addition, this system can be used to develop adenoviral vectors with modified tropism for cell-specific targeting.

The present invention further discloses the development of a targeted adenovirus created by ablating endogenous viral tropism and introducing novel tropism. These two goals were achieved by employing a neutralizing anti-fiber antibody, or antibody fragment, chemically conjugated to a cell-specific ligand. The folate receptor which is overexpressed on the surface of a variety of malignant cells was used. Therefore, folate was conjugated to the neutralizing Fab fragment of an anti-fiber monoclonal antibody. This Fab-folate conjugate was complexed with an adenoviral vector carrying the luciferase reporter gene and was shown to redirect adenoviral infection of target cells via the folate receptor at a high efficiency. Furthermore, when complexed with an adenoviral vector carrying the gene for herpes simplex virus thymidine kinase, the Fab-folate conjugate mediated the specific killing of cells which overexpress the folate receptor. The present invention thus represents the first demonstration of the retargeting of a recombinant adenoviral vector via a non-adenoviral cellular receptor.

In another embodiment of the present invention, there is provided a fiber rescue system useful in constructing adenoviral vectors possessing modified fiber genes, said adenoviral vectors modified by introducing ligands into the target cell binding domains of the adenoviral fiber so as to modify viral tropism, said fiber rescue system comprising: (a) a fiber shuttle plasmid containing: (1) a plasmid origin of replication, (2) an antibiotic resistance gene, and (3) a fragment of an adenoviral genome containing the fiber gene and flanking DNA sequences; and (b) a rescue plasmid containing: (1) a complete copy of the circularized adenovirus genome and the adenoviral fiber gene replaced by a plasmid origin of replication and antibiotic resistance gene, wherein said fiber shuttle plasmid is co-transfected with said rescue plasmid into a host cell; and wherein an intact viral genome is obtained by performing homologous DNA recombination between homologous regions of the shuttle plasmid and the rescue plasmid providing a modified adenovirus with an modified fiber gene.

In another embodiment of the present invention, there is provided a method of making a recombinant adenovirus having a modified fiber gene, comprising the steps of: incorporating a plasmid origin of replication, an antibiotic resistance gene, and a fragment of an adenoviral genome containing the fiber gene and flanking DNA sequences into a fiber shuttle plasmid; constructing a rescue plasmid comprising a plasmid origin of replication, an antibiotic resistance gene, and a complete copy of the circularized adenovirus genome and the adenoviral fiber gene replaced by a plasmid origin of replication and antibiotic resistance gene; co-transfecting said fiber shuttle vector with said rescue plasmid into a host cell; obtaining an intact viral genome by performing homologous DNA recombination between homologous regions of the shuttle plasmid and the rescue plasmid so as to generate a modified adenovirus with an intact fiber gene.

In yet another embodiment of the present invention, there is provided a targeted adenovirus lacking endogenous viral tropism but having a novel tropism, said adenovirus comprising: (1) a neutralizing anti-fiber antibody, or antibody fragment, or fusions thereof, linked to a cell specific attachment moiety to form a conjugate; and (2) an adenoviral vector containing a reporter gene, wherein said conjugate is complexed with said vector to form a targeted adenovirus redirected to infect target cells via the cell-specific ligand.

In still yet another embodiment of the present invention, there is provided a method of making a targeted adenovirus lacking endogenous viral tropism but having a novel tropism, comprising the steps of: linking a neutralizing anti-fiber antibody, or antibody fragment, or fusions thereof, to a cell specific attachment moiety to form a conjugate; and complexing said conjugate with an adenoviral vector containing a reporter gene so as to form a recombinant adenoviral vector which can bind to a target cell via a non-adenoviral cellular receptor.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4 shows an evaluation of adenoviral fiber protein variants.

FIG. 12A shows the predicted map of restriction endonuclease recognition sites for Ad5luc3 and the fiber variant derivative, Ad5luc3.FSP. FIG. 12B shows an analysis of genomic DNA derived from Ad5luc3 (lane 2) and Ad5luc3.FSP (lane 3) by restriction endonuclease digestion with FspI. Lane 1 represents DNA size markers. Arrowheads indicate FspI restriction fragments of 11, 8 and 3 kb. The 11 kb fragment in the Ad5luc3 FspI digest (lane 2) is replaced by 8 and 3 kb fragments in the Ad5luc3.FSP digest (lane 3), indicating the presence of a novel restriction site in the recombinant genome.

FIG. 14A: Predicted maps of DraI and ScaI restriction endonuclease recognition sites for Ad5-Luc 3 and Ad5/3-Luc 3. The filled box represents the fiber gene. FIG. 14B: Analysis of genomic DNA derived from Ad5-Luc 3 and Ad5/3-Luc 3. Lane 1: Ad5-Luc 3—ScaI; lane 2: Ad5/3-Luc 3—ScaI; lane 3: 1 kb marker; lane 4: Ad5-Luc 3—DraI; lane 5: Ad5/3-Luc 3—DraI. Arrowheads indicate restriction fragments of 24.5, 12.6, 9.8, 3 and 2.8 kb.

DETAILED DESCRIPTION OF THE INVENTION

Definitions

Figure 1:
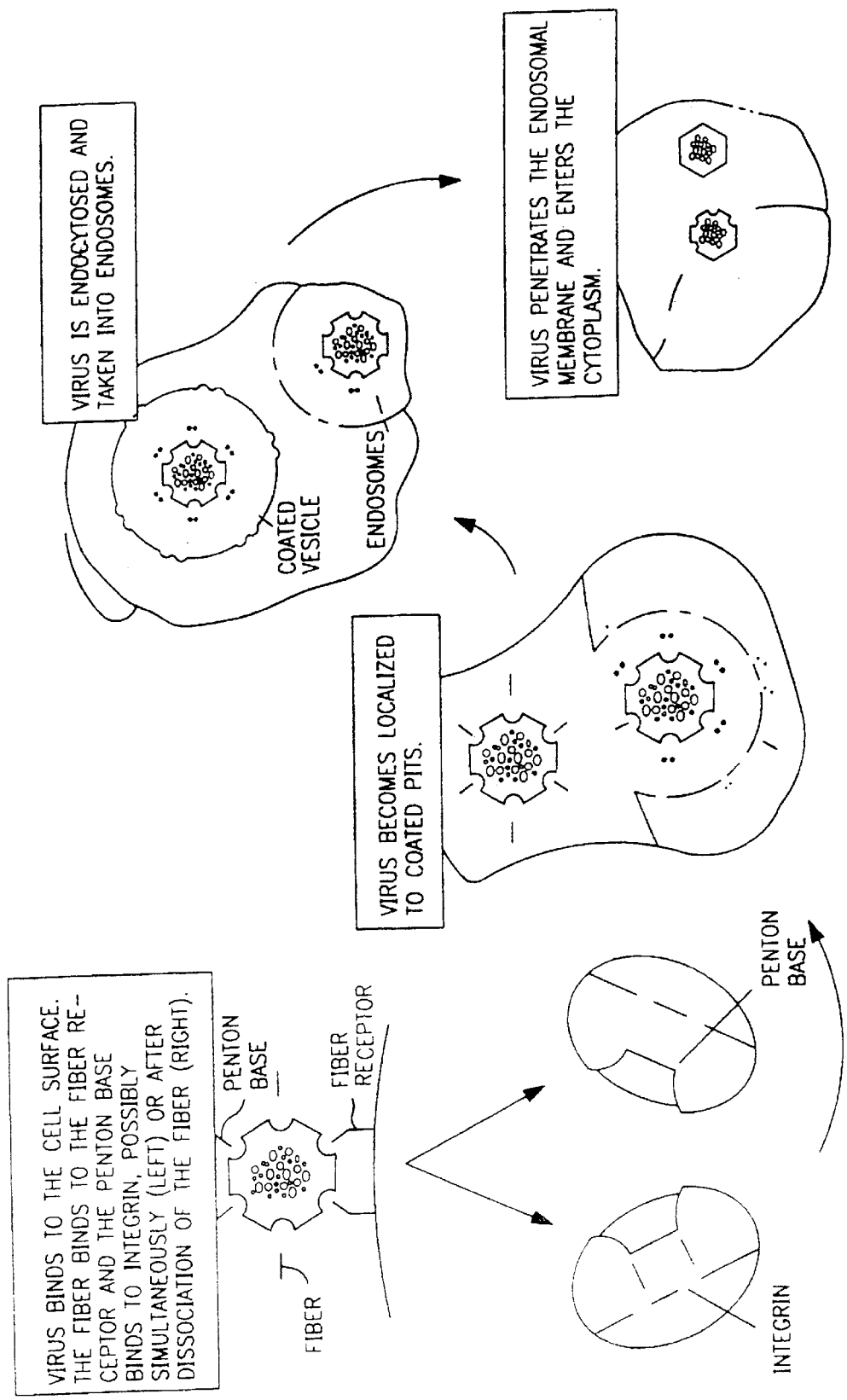
FIG. 1 shows the pathway of adenovirus entry into cells.

As used herein, the terms "fiber gene" and "fiber variant" refers to the gene encoding the adenovirus fiber protein and a modification thereof.

As used herein, the term "fiber rescue plasmid," refers to a plasmid which lacks a viable fiber gene, after homologous recombination with another plasmid but can acquire such.

As used herein, the term "shuttle plasmid or shuttle vector" refers to a plasmid which can contribute a viable fiber gene to a fiber deficient rescue plasmid.

As used herein, the term "silent mutation" refers to a mutation which does not change the protein encoded by the gene's open reading frame.

As used herein, the term "mature trimeric fiber" refers to a fiber which possesses the native tertiary conformation.

As used herein, the term "peptide linker" refers to short peptide serving as a spacer between the fiber and the ligand.

As used herein, the term "physiologic ligand" refers to a ligand for a cell surface receptor.

As used herein, the term "stuffer segment" refers to irrelevant DNA used to create functionally relevant spacing of a plasmid.

It is an object of the present invention to expand the tropism of adenoviruses by incorporating novel ligands into the fiber cell binding domain without requiring the means to incorporate the modified fiber into mature virions.

It is an object of the present invention to modify the tropism of recombinant adenoviral vectors using genetic methods to alter the adenoviral fiber cell-binding protein.

It is another object of the present invention to generate an adenovirus with modified fiber gene using a two-plasmid rescue system for derivation of adenoviral fiber recombinants.

It is an additional object of the present invention to design a fiber rescue system to allow construction of adenoviral vectors possessing modified fiber genes. Using such a fiber rescue system, a person with ordinary skill in this art would be able to accomplish the introduction of ligands into the target cell binding domains of the adenoviral fiber to modify viral tropism.

In accordance with the above-mentioned objects, there is provided by a fiber rescue system useful in constructing adenoviral vectors possessing modified fiber genes, said adenoviral vectors modified by introducing ligands into the target cell binding domains of the adenoviral fiber so as to modify viral tropism, said fiber rescue system comprising: (a) a fiber shuttle plasmid containing: (1) a plasmid origin of replication, (2) an antibiotic resistance gene, and (3) a fragment of an adenoviral genome containing the fiber gene and flanking DNA sequences; and (b) a rescue plasmid containing: (1) a complete copy of a circularized adenovirus genome and the adenoviral fiber gene replaced by a plasmid origin of replication and antibiotic resistance gene, wherein said fiber shuttle plasmid is co-transfected with said rescue plasmid into a host cell; and wherein an intact viral genome is obtained by performing homologous DNA recombination between homologous regions of the shuttle plasmid and the rescue plasmid providing a modified adenovirus with an modified fiber gene.

In the fiber rescue system of the present invention, the plasmid origin of replication and the antibiotic resistance gene would be well known to those having ordinary skill in this art. As will be apparent to those in this art, the fiber rescue system of the present invention, the fiber rescue plasmid may also contain a gene encoding a therapeutic protein.

The present invention is also directed to a method of making a recombinant adenovirus having a modified fiber gene, comprising the steps of: incorporating a plasmid origin of replication, an antibiotic resistance gene, and a fragment of an adenoviral genome containing the fiber gene and flanking DNA sequences into a fiber shuttle plasmid; inserting a plasmid origin of replication, an antibiotic resistance gene, a complete copy of a circularized adenovirus genome and the adenoviral fiber gene replaced by a plasmid origin of replication and antibiotic resistance gene into a rescue plasmid; co-transfecting said fiber shuttle vector with said rescue plasmid into a host cell; obtaining an intact viral genome by performing homologous DNA recombination between homologous regions of the shuttle plasmid and the rescue plasmid so as to generate a modified adenovirus with an intact fiber gene. The fiber rescue plasmid may further contain a gene encoding a therapeutic protein. The modified adenovirus fiber as prepared herein retains its ability to trimerize and retains its native biosynthesis profile.

The present invention is also directed to a targeted adenovirus lacking endogenous viral tropism but having a novel tropism, said adenovirus comprising: (1) a neutralizing anti-fiber antibody, or antibody fragment, or fusions thereof, linked to a cell specific attachment moiety to form a conjugate; and (2) an adenoviral vector containing a reporter gene, wherein said conjugate is complexed with said vector to form a targeted adenovirus redirected to infect target cells via the cell-specific ligand. Preferably, the cell specific attachment moiety is selected from the group consisting of physiological ligands, anti-receptor antibodies or cell specific peptides. In addition, the adenoviral vector may further contain a therapeutic gene. In one embodiment, the therapeutic gene is the herpes simplex virus-thymidine kinase gene.

The present invention is also directed to a method of making a targeted adenovirus lacking endogenous viral tropism but having a novel tropism, comprising the steps of: linking a neutralizing anti-fiber antibody, or antibody fragment, or fusions thereof, to a cell specific attachment moiety to form a conjugate; and complexing said conjugate with an adenoviral vector containing a reporter gene so as to form a recombinant adenoviral vector which can bind to a target cell via a non-adenoviral cellular receptor.

The present invention is also directed to a method of killing tumor cells in an individual in need of such treatment, comprising the steps of: pretreating said individual an effective amount of the adenoviral vector of the present invention; and administering ganciclovir to said individual.

Mechanisms by which adenoviruses accomplish infection

Following intravenous administration of the adenovirus vector, three distinct sequential steps are required for targeted expression of the therapeutic gene in specific cells: (1) attachment of the adenovirus vector to specific receptors on the surface of the target cell; (2) internalization of the virus; and (3) transfer of the gene to the nucleus where it can be expressed. Thus any attempt to modify the tropism of an adenovirus vector must retain its ability to perform these three functions efficiently. Furthermore, the modification of adenovirus tropism must be approached with knowledge of the biology of adenovirus infection (FIG. 1). It has recently been shown that the globular carboxy-terminal "knob" domain of the adenovirus fiber protein is the ligand for attachment to the adenovirus cellular receptor, the first step in infection. A trimeric fiber protein protrudes from each of the 12 vertices of the icosahedral viral particle where it is attached noncovalently to the penton base. The amino-terminal tail is separated from the knob domain by a long rod-like shaft comprising a 15-amino acid residue motif repeated 22 times in human adenovirus types 2 and 5. The knob is both necessary and sufficient for virion binding to host cells. Following attachment, the next step in adenovirus infection is internalization of the virion by receptor-mediated endocytosis. This process is mediated by the interaction of Arg-Gly-Asp (RGD) sequences in the penton base with secondary host cell receptors, integrins avb3 and avb5. Post-internalization, the virus is localized within the cellular vesicle system, initially in clathrin-coated vesicles and then in cell endosomes. Acidification of the endosomes allows the virions to escape and enter the cytosol. This step has been hypothesized to occur via a pH-induced alteration in the hydrophobicity of the adenoviral capsid proteins which allows their interaction with the cell vesicle membrane. The virion then localizes to the nuclear pore and its genome is translocated to the nucleus of the host cell. This understanding of the adenovirus entry pathway is required to modify the tropism of adenoviral vectors to permit the targeting of specific cell types.

Adenoviral cellular binding and internalization uncoupled from subsequent steps in infection Modification of the tropism of the adenoviral vector so that it recognizes and binds to a novel receptor on specific target cells requires that the vector still be able to accomplish the distal steps of internalization and gene transfer. The basic design of a molecular conjugate vector consists of plasmid DNA attached to a macromolecule ligand which can be internalized by the cell type of interest. To accomplish this, a molecular conjugate vector contains two distinct functional domains: a DNA binding domain which is composed of a polycation such as polylysine and a ligand domain which binds to a specific cell surface receptor. The efficiency of gene transfer was idiosyncratic due to endosome-entrapment of the conjugate-DNA complex after internalization. To overcome this limitation, a replication-deficient adenovirus was incorporated into the conjugate design to capitalize on its ability to accomplish endosome disruption. Incorporation of the adenovirus into the vector configuration dramatically augmented the gene transfer efficiency of the vector based upon the ability of the complex to avoid entrapment in the cell vesicle system. However, the introduction of the adenovirus into the system undermined one of the theoretical attributes of this vector: the ability to accomplish targeted, cell-specific gene delivery based upon the incorporated ligand domain. To overcome this limitation, an anti-fiber antibody was derived which could specifically block adenoviral binding and entry into target cells. It was hypothesized that coating the complex with antibody would block adenoviral binding, thus permitting targeted gene delivery exclusively via the ligand domain. In these studies, it was shown that the use of antibody-coated, binding-incompetent adenovirus did not decrease the overall levels of gene expression observed. Despite entry via an alternate internalization pathway, fiber binding was not required for the adenovirus to mediate endosomal vesicle disruption being routed through a non-adenoviral pathway, the virus accomplished efficient post-internalization entry events. Hence, the processes of adenoviral binding and subsequent entry steps are not functionally linked. It should therefore be possible to reroute recombinant adenoviral vectors through heterologous cellular entry pathways in a similar manner while retaining their desirable downstream entry properties.

The ability of adenoviral vectors to accomplish efficient gene transfer after internalization through a non-adenoviral entry pathway would be of particular importance in gene therapy. In this regard, it has been shown that the ability of adenoviral vectors to transduce mature muscle fibers is very poor, no greater than in vivo transduction by naked DNA. This phenomenon has been correlated with a developmental downregulation of the adenoviral internalization receptors, integrins avb3 and avb5, in mature muscle cells. This problem could therefore be resolved by achieving internalization of the adenovirus vector by an alternate pathway independent of these integrins.

Tropism-modified viral vectors constructed to achieve targeted cell-specific gene delivery Attempts to modify the tropism of adenoviral vectors must be considered in the light of strategies which have been utilized to modify the cell-binding specificity of other viral vectors. In this context, most work to date has focused on altering retroviral vectors to allow cell-specific transduction. Infection of host cells with retroviral vectors results from specific binding of the viral envelope glycoprotein to receptor molecules on the cell surface. The host and tissue specificity of a retroviral vector are defined by the cell surface receptors which it is able to recognize. Thus, ecotropic retroviruses can only infect cells of one species, or even only one cell-type of one species. Conversely, amphotropic retroviruses have a broad host range and can infect different cell types of different species. These differences are a result of structural variations of the envelope glycoprotein which determine the binding specificity for cellular receptors. Therefore, targeting of retroviral vectors has been attempted by introducing alternate envelope glycoproteins or modifying the retroviral envelope glycoprotein to confer new binding specificity.

There are two aspects to consider in the modification of adenoviral tropism: (1) ablation of endogenous tropism; and (2) introduction of novel tropism. It is necessary for adenoviruses to retain their endogenous tropism in order to form plaques in normal packaging cell lines. Disclosed herein is the creation of a tropism-expanded adenoviral vector; that is, a vector with the capacity to achieve binding to a non-native receptor which would allow cell-specific gene transfer after systemic in vivo delivery. After achieving this goal, it would then become practically feasible to accomplish the ablation of native tropism.

The following examples are given for the purpose of illustrating various embodiments of the invention and are not meant to limit the present invention in any fashion.

Figure 2:
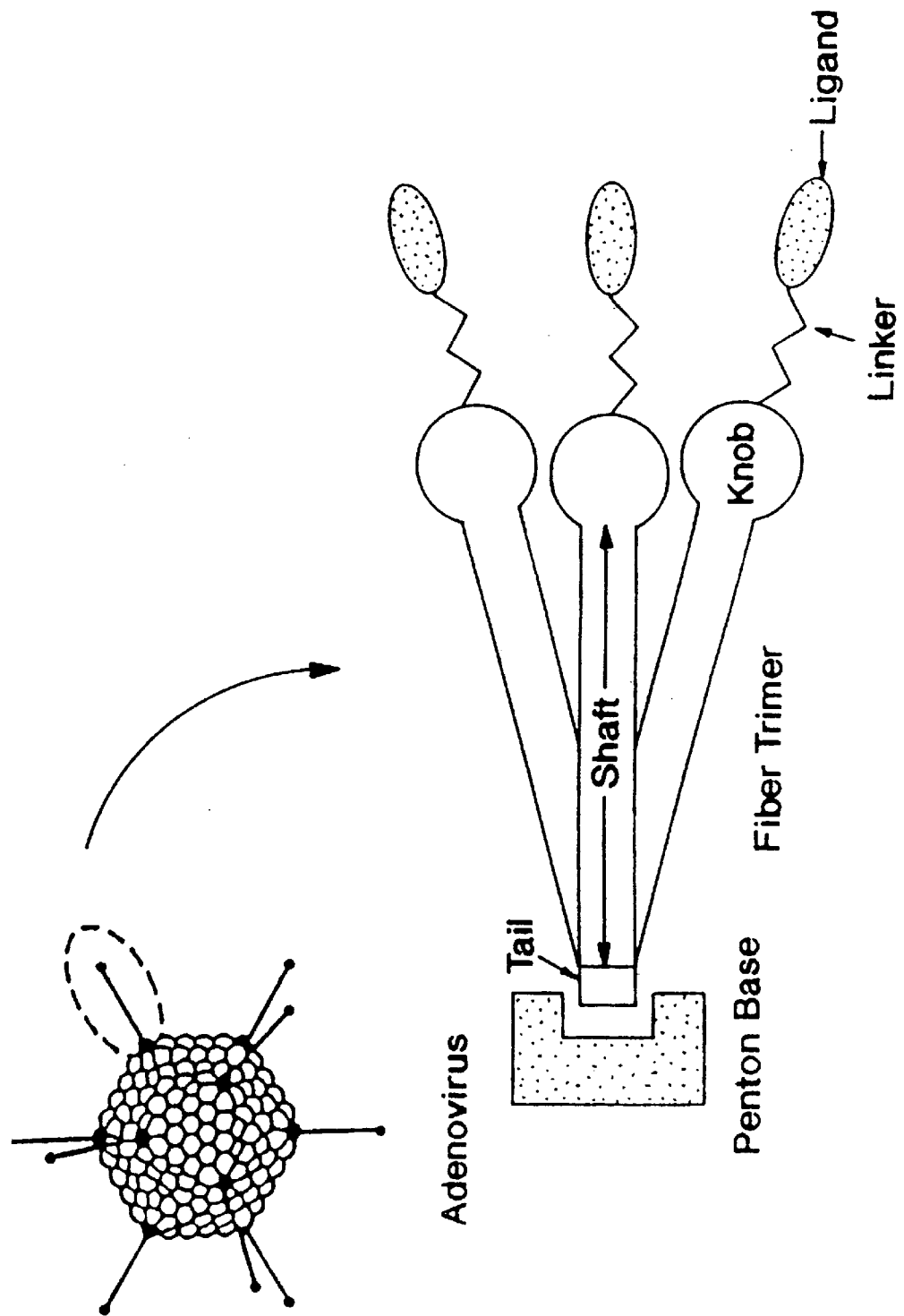
FIG. 2 shows the strategy to incorporate a heterologous peptide ligand at the knob domain of adenoviral fiber. This strategy involves the genetic modification of the fiber to generate a chimeric protein consisting of mature trimeric fiber, peptide linker, and an added physiologic ligand at the knob domain to target the adenovirus into heterologous cellular entry pathways.

EXAMPLE 1
Modifying the tropism of recombinant adenoviral vectors by genetic methods to alter the adenovirus fiber cell-binding protein One strategy to derive a tropism-modified recombinant adenovirus is directed towards genetic modification of the fiber protein to accomplish incorporation of heterologous cell-binding ligands, which could then mediate adenoviral entry by alternate receptor pathways. This approach capitalizes on the knowledge that the endogenous cell-binding ligand of adenovirus is localized within the knob portion of the fiber protein. The strategy was therefore to localize the novel cell-binding ligand in the analogous position, thereby accomplishing two goals: (1) the novel cell-binding ligand would be localized in the region of the endogenous ligand, which is likely to be favorable for interaction with the cognate cellular receptor; and (2) the novel-cell binding ligand would be removed from other adenoviral capsid proteins, whose function might be important in distal, post-binding entry functions. The genetic incorporation of heterologous peptides required consideration of the strict structural limitations of the fiber quaternary configuration. In this regard, the fiber protein is synthesized initially as a monomer which self-trimerizes by virtue of intermolecular, non-covalent interactions, initiated at the carboxy terminus of the molecule. After trimerization, the amino terminus of the native fiber can insert into the penton base. Thus, additions to the knob portion of the fiber, corresponding to the carboxy terminus of the molecule, could potentially impair trimer formation and prevent incorporation of chimeric fiber molecules into the mature adenoviral capsid. In addition to these considerations, it was important to achieve a final quaternary configuration whereby the incorporated ligand was localized on the exterior of the mature fiber trimer. Hence, it was not apparent that added ligands would be localized outside the molecular structure of the knob and thus accessible to achieve target cell binding. With these considerations in mind, fiber-ligand fusion proteins were created by genetically incorporating into the fiber gene heterologous sequences encoding peptides with physiologic ligand functions (FIG. 2).

The initial analysis confirmed that: (1) the fiber fusion genes produce a chimeric fiber molecule capable of maturing into a normal trimeric quaternary configuration; and (2) the fiber fusion genes express a chimeric fiber molecule whereby the heterologous ligand is localized on the exterior of the trimeric molecule. Achievement of these goals, even in a limited context, predicts that further analysis would identify the optimal ligands from the standpoints of cell binding and internalization.

EXAMPLE 2
Construction of a fiber gene encoding a peptide ligand

Figure 3:
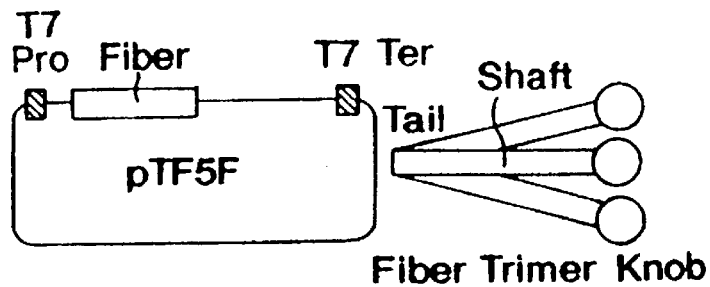
FIG. 3 shows a schematic of fiber-GRP ligand fusion protein construction. T7 vaccinia expression vectors were constructed to contain wild-type fiber of adenovirus type 5 only (pTF5F), fiber and ten amino acid linker only (pTF5FB), and the fiber-GRP fusion construct (pTF5FB-GRP). T7 Pro: T7 promoter; T7 Ter: T7 RNA polyerase transcription termination site; B: BamH1 restriction site.
Figure 3:
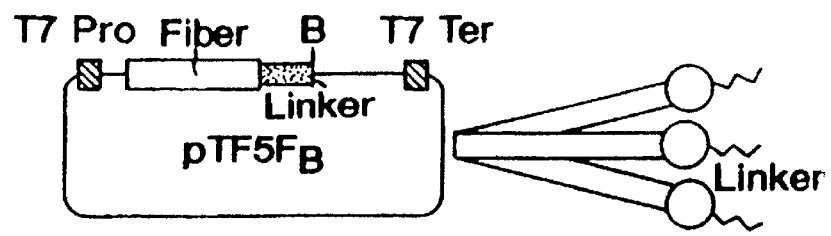
Figure 3:
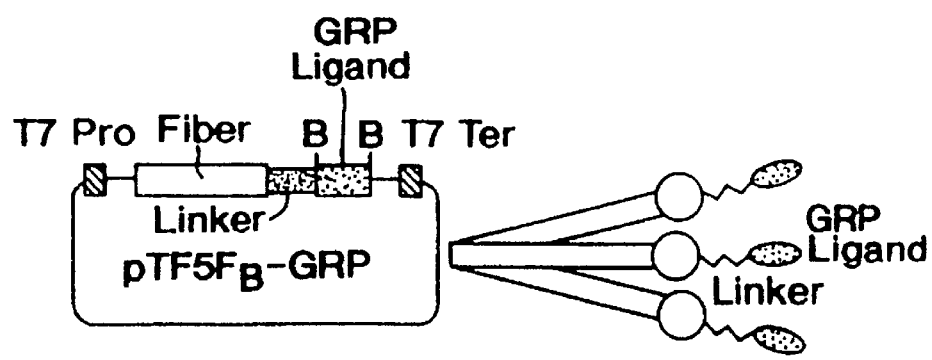

The first step in the creation of a fiber-ligand fusion protein was site-directed mutagenesis of the 3' end of the wild-type adenovirus type 5 fiber gene which had been cloned into the T7 vaccinia expression vector pTF7.5 under the control of the T7 promoter, resulting in vector pTF5F (FIG. 3). A unique BamHI restriction site was introduced at the 3' end of the fiber gene to facilitate subsequent cloning of oligonucleotides encoding the test ligands. Sequences encoding a 10 amino acid linker region (ProSerAlaSerAlaSerAlaSerAlaPro) were then inserted immediately upstream of the BamHI site to: (1) minimize any possible steric constraints between the fiber protein and the heterologous peptide to be added; and (2) present the test ligand extended away from the body of the fiber protein. The vector containing this modified fiber gene was designated pTF5FB. A fiber-ligand fusion gene was engineered by cloning sequences encoding the terminal decapeptide of the gastrin-releasing peptide, GRP, into the BamHI site, resulting in vector pTF5FB-GRP. This ligand was chosen because of: (1) its small size; and (2) its ability to be internalized into its target cell by receptor-mediated endocytosis.

EXAMPLE 3
Expression of genetically modified fiber protein

In order to express the wild-type or modified fiber proteins, 80% confluent HeLa cells in Opti-MEM1 reduced serum medium (Gibco-BRL) were first incubated for 1 hour at 37° C. with a recombinant vaccinia virus which expresses T7 RNA polymerase. The infected cells were then transfected with vectors pTF5F, pTF5FB or pTF5FB-GRP using Lipofectin (Gibco-BRL) according to the manufacturer's instructions. After 24 hours, cells were washed with phosphate-buffered saline, pH 7.4 (PBS) and scraped into Tris-EDTA buffer, (10 mM Tris-HCl, 1 mM EDTA; pH 8.0) prior to sonication for a total of 2 minutes. Clarified lysates were used as the source of recombinant fiber.

To confirm the expression of a fiber-GRP fusion protein, lysates from vaccinia-infected HeLa cells which had been transfected either with plasmid pTF5FB or with plasmid pTF5FB-GRP were immunoprecipitated according to standard techniques with a mouse monoclonal anti-fiber antibody (4D2, 2A6 or AF7A) or with a rabbit anti-human GRP antibody (DAKOPATTS). The immune complexes were resuspended in 2× SDS-PAGE sample buffer containing urea and denatured by boiling before being electrophoresed on a 10% SDS-polyacrylamide gel. The separated proteins were transferred on to a PVDF membrane (BioRad Laboratories) and probed with either anti-fiber antibody 4D2 or anti-GRP antibody. An alkaline phosphatase-conjugated goat anti-mouse or -rabbit antibody (Southern Biotechnology) was employed as the secondary antibody prior to detection with NBT/BCIP.

Figure 4A:
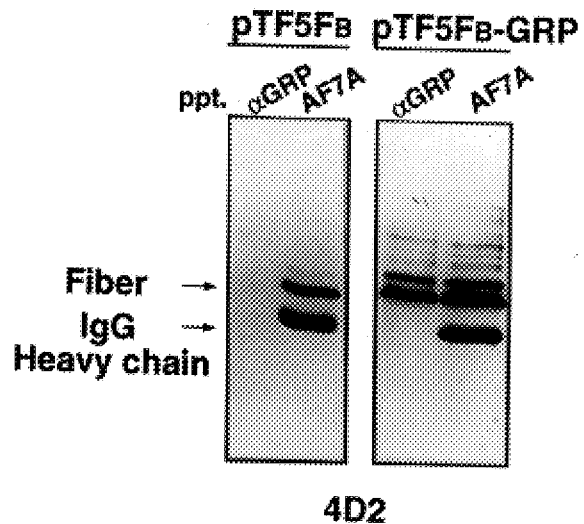
FIG. 4A shows HeLa cell lysates transfected with fiber fusion constructs were immunoprecipitated with anti-GRP or anti-fiber AF7A antibodies. Western blots were then performed on boiled samples using anti-fiber mAb 4D2.
Figure 4B:
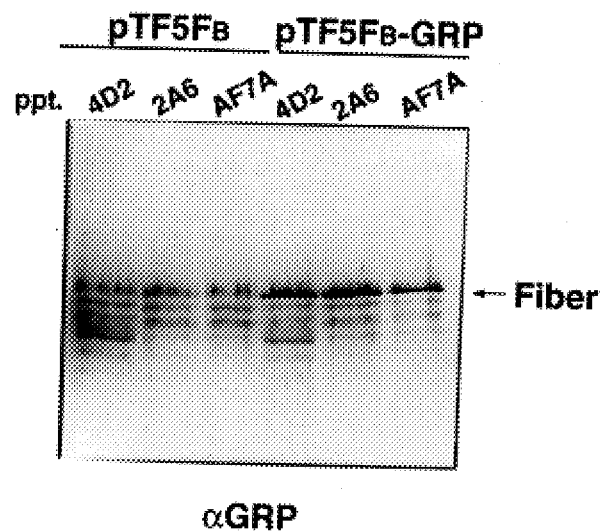
FIG. 4B shows lysates of HeLa cell transfected with fiber fusion constructs were immunoprecipitated with three anti-fiber antibodies: 4D2, AF7A, and 2A6. Western blots were then probed with an anti-GRP antibody.

As shown in FIG. 4A, a protein precipitated with the anti-GRP antibody from HeLa cells transfected with plasmid pTF5B-GRP, which encodes the fiber-GRP construct, is the size of the mature fiber and is recognized by an anti-fiber mAb. This protein was identical in size to the protein precipitated from pTF5B-GRP-transfected cells with mAb AF7A, which recognizes fiber trimers only. Moreover, the anti-GRP antibody failed to precipitate a protein of similar size from HeLa cells transfected with plasmid pTF5B, which encodes the fiber-linker construct only. These results indicate that plasmid pTF5B-GRP expressed a fiber-GRP fusion protein. To confirm this, lysates from HeLa cells transfected with plasmid pTF5B-GRP or pTF5B were immunoprecipitated with the three different anti-fiber mAbs prior to Western blot analysis with the anti-GRP antibody. FIG. 4B shows that a protein recognized by both anti-fiber and anti-GRP antibodies was present in the lysate of HeLa cells transfected with plasmid pTF5B-GRP, which encodes the fiber-GRP construct, but was absent from the lysate of HeLa cells transfected with plasmid pTF5B. Thus, this construct was capable of expressing a fiber-GRP fusion protein in a eukaryotic system.

EXAMPLE 4

Quaternary structure of fiber protein variants in vaccinia vector-infected cells Correct fiber protein folding is absolutely required for incorporation of the fiber protein into the vertices of nascent adenovirus capsids. Since the aim is to construct a recombinant adenovirus with a genetically modified fiber, it was first important to determine whether incorporation of exogenous peptides to the carboxy terminus of fiber still allowed proper fiber protein folding into the native quaternary configuration. Preservation of the quaternary structure or trimerization of the fiber-ligand fusion protein would theoretically be indicative of proper adenovirus capsid assembly with the modified fiber proteins.

Figure 5:
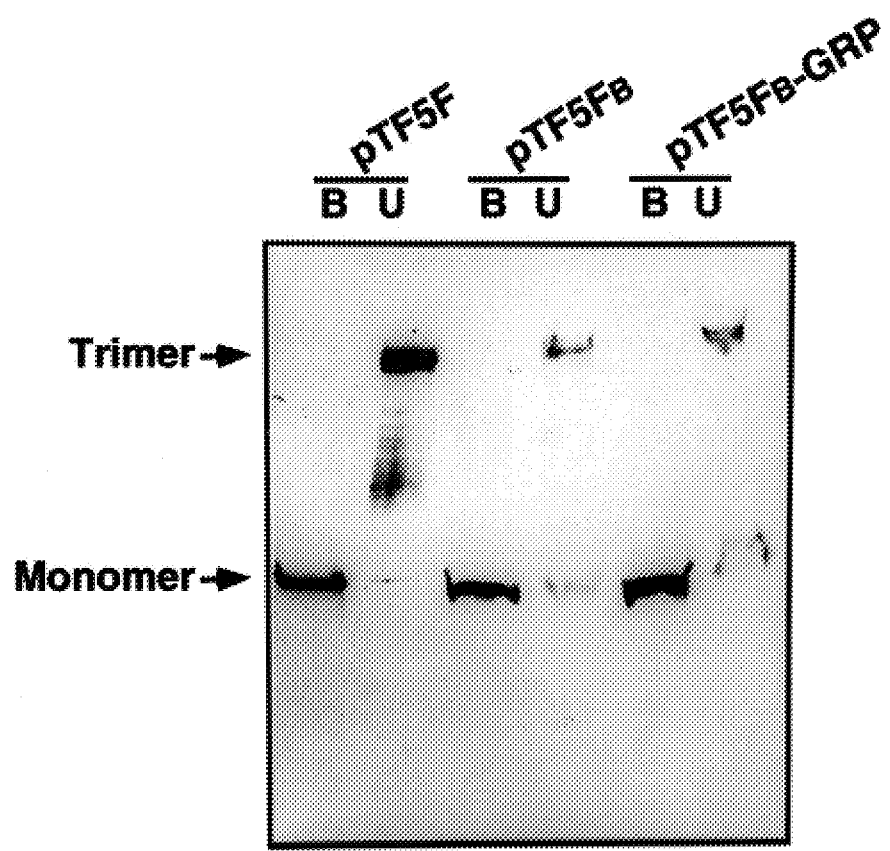
FIG. 5 shows a determination of the quaternary structure of the fiber-GRP fusion protein. Boiled and unboiled HeLa cell lysates transfected with three fiber constructs were analyzed by western blot using anti-fiber mAb 4D2 which recognizes both fiber monomers and trimers.

To determine the quaternary structure of the fiber protein variants, boiled and unboiled samples of lysates of HeLa cells transfected with plasmids pTF5F, pTF5FB or pTF5FB-GRP were electrophoresed on a 4–20% gradient Tris-Cl gel. Upon boiling, the fiber protein is dissociated to a monomeric form, whereas unboiled fiber migrates as a trimer. The separated proteins were transferred to a PVDF membrane and subjected to Western blot analysis employing anti-fiber mAb 4D2 which recognizes both fiber monomers and trimers. FIG. 5 shows that boiled fiber-GRP fusion protein migrated as the monomeric form of the protein whereas unboiled fiber-GRP fusion protein migrated as a trimer. This indicates that it is possible to add exogenous sequences to the carboxy terminus of the fiber protein, at least as large as twenty-two amino acids, without perturbing the quaternary structure of the protein. Thus, the derived fiber-ligand fusion gene retains the requisite quaternary configuration characteristics for its incorporation into assembled adenoviral capsids.

EXAMPLE 5

Biosynthesis of fiber protein variants in vaccinia vector-infected cells

Figure 6:
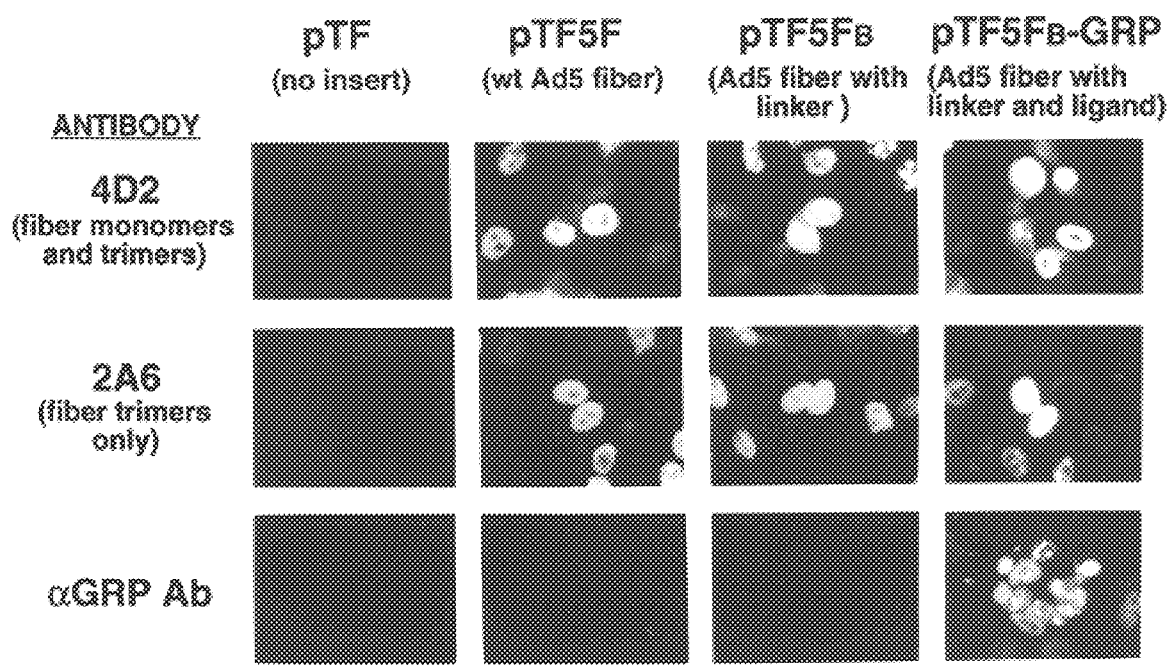
FIG. 6 shows the biosynthesis of the fiber-GRP fusion protein. HeLa cells seeded on glass coverslips were transfected with four different T7 expression vectors. After 24 hours, the HeLa cells were fixed, permeabilized, and incubated with anti-fiber mAb 4D2 which recognizes both fiber monomers and trimers, anti-fiber mAb 2A6 which recognizes fiber trimers only, or a polyclonal antibody directed against the GRP peptide.

In order for the fiber protein to be properly incorporated into the vertices of adenoviral capsids it must be transported from the cytoplasm to the nucleus, where it accumulates prior to virion assembly. To determine whether the fiber-GRP fusion protein was able to achieve nuclear localization, HeLa cells seeded on glass coverslips were transfected with plasmids pTF, the parental vector, pTF5F, which expresses wild-type fiber, pTF5FB, which expresses the fiber-linker construct, or pTF5FB-GRP, which expresses the fiber-GRP ligand construct. After 24 hours, the cells were fixed with 3% (v/v) paraformaldehyde in PBS, pH 7.4, and permeabilized with methanol prior to analysis by indirect immunofluorescence with anti-fiber mAbs 4D2 and 2A6 or an anti-GRP antibody being used as the primary antibodies. FITC-conjugated goat anti-mouse or -rabbit antibody (Sigma) was employed as the secondary antibody and fluorescent cells were visualized under a fluorescence microscope (FIG. 6).

Fluorescent staining of the nuclei of HeLa cells transfected with plasmids pTF5F, pTF5FB and pTF5FB-GRP was observed when anti-fiber mAbs were used as the primary probes. Further, when anti-GRP antibody was employed, nuclear fluorescence was only detected in HeLa cells transfected with pTF5B-GRP. These findings demonstrate that the fiber-GRP fusion protein correctly localized to the nucleus of cells in which it was expressed. Therefore it is possible to add exogenous sequences to the carboxy terminus of the fiber protein without perturbing the pattern of biosynthesis of the protein.

EXAMPLE 6

Accessibility of the GRP ligand in the native form of the fiber-GRP fusion protein Having demonstrated that it is possible to add short peptide sequences to the carboxy terminus of the adenovirus fiber protein without impairing either the biosynthesis or the proper folding of the protein, it was determined whether the GRP ligand is localized on the fiber protein externally as desired. If the GRP ligand, or any other ligand, is used to redirect adenoviral vectors, it is imperative that the ligand be externally accessible to its cellular receptor. In order to determine whether the GRP ligand in the trimeric form of the fiber-GRP fusion protein was exposed, an immunoblot assay was performed. Boiled and unboiled lysates from HeLa cells transfected with pTF5FB or pTF5FB-GRP were probed with either anti-fiber mAb 4D2, which recognizes both fiber trimers and monomers, or anti-GRP antibody. In this assay, unboiled lysates should have intact trimeric fiber proteins, while boiling denatures this quaternary structure, yielding monomers.

Figure 7:
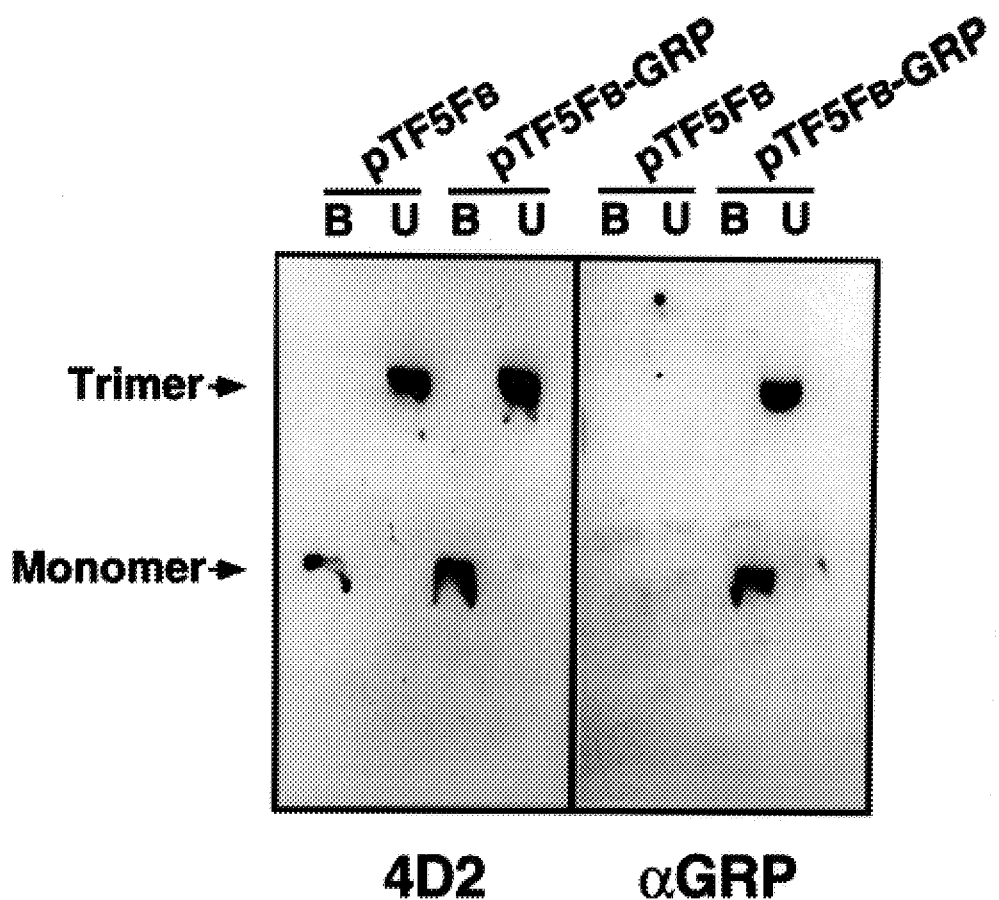
FIG. 7 shows the accessibility of the GRP ligand in the fiber-GRP trimer. To determine whether the GRP ligand in the native form of the fiber-GRP fusion protein was accessible to binding, an immunoblot assay was performed. Boiled (B) and unboiled (U) HeLa cell lysates transfected with either pTF5FB or pTF5FB-GRP were separated by SDS-PAGE, transferred to a PVDF membrane and probed with anti-fiber mAb 4D2 or anti-GRP antibodies.

As shown in FIG. 7, when boiled and unboiled lysates containing the modified fiber with the linker only (pTF5FB) were subjected to Western blot analysis and probed with 4D2, a monomer and trimer band were detected for the boiled and unboiled samples, respectively. When the same samples were probed with anti-GRP antibody, no bands could be detected, due to the absence of ligand in this construct. When boiled and unboiled cell lysates containing the fiber-GRP fusion protein were probed with 4D2, a monomer and trimer band were detected, respectively. When the same samples were probed with an anti-GRP antibody, a monomer band could be detected in the boiled sample and a trimer band could be detected in the unboiled sample. These results indicate that not only is the GRP ligand in the fiber-GRP fusion protein accessible to binding in the monomeric form of the protein, but the ligand is also exposed and accessible to binding in the native or trimeric form of the protein.

These studies demonstrated several properties of the fiber-ligand fusion protein, including that (1) the protein retains its ability to trimerize; (2) the protein retains its native biosynthesis profile; and (3) the protein presents the added ligand in an exterior, surface-exposed localization. These studies demonstrate the feasibility of introducing heterologous peptide ligands into the cell-binding domain of the adenoviral fiber protein in a manner consistent with the derivation of functional chimeric adenoviral particles.

EXAMPLE 7

Modifying the tropism of recombinant adenoviral vectors using genetic methods to alter the adenoviral fiber cell-binding protein The tropism of recombinant adenoviral vectors has been altered by incorporating heterologous ligands into the fiber protein by creating genetic fusion constructs. The data presented above shows the incorporation small peptide ligands into the carboxy terminus of the adenoviral fiber protein. The limits of ligand size which can be incorporated in this manner can be determined. Whereas a small peptide (GRP) was initially incorporated as a novel ligand domain for the fiber, other types of ligands, of larger size and more complex configuration, need to be incorporated into a chimeric fiber to achieve a tropism-modified adenoviral vector useful for gene therapy. Conventional recombinant-DNA methodologies would not be amenable to facile derivation of recombinant adenoviral genomes incorporating the chimeric fiber genes for functional screening purposes. Therefore, the alternate methodology of the present invention was developed which allows rapid construction of fiber-modified virions. These vectors are confirmed for the successful incorporation of chimeric fiber proteins with distinct target binding specificities. These studies result in the derivation of a series of tropism-modified adenoviral vectors based upon genetic modification of the fiber protein.

EXAMPLE 8

Construction of recombinant plasmids

Figure 8:
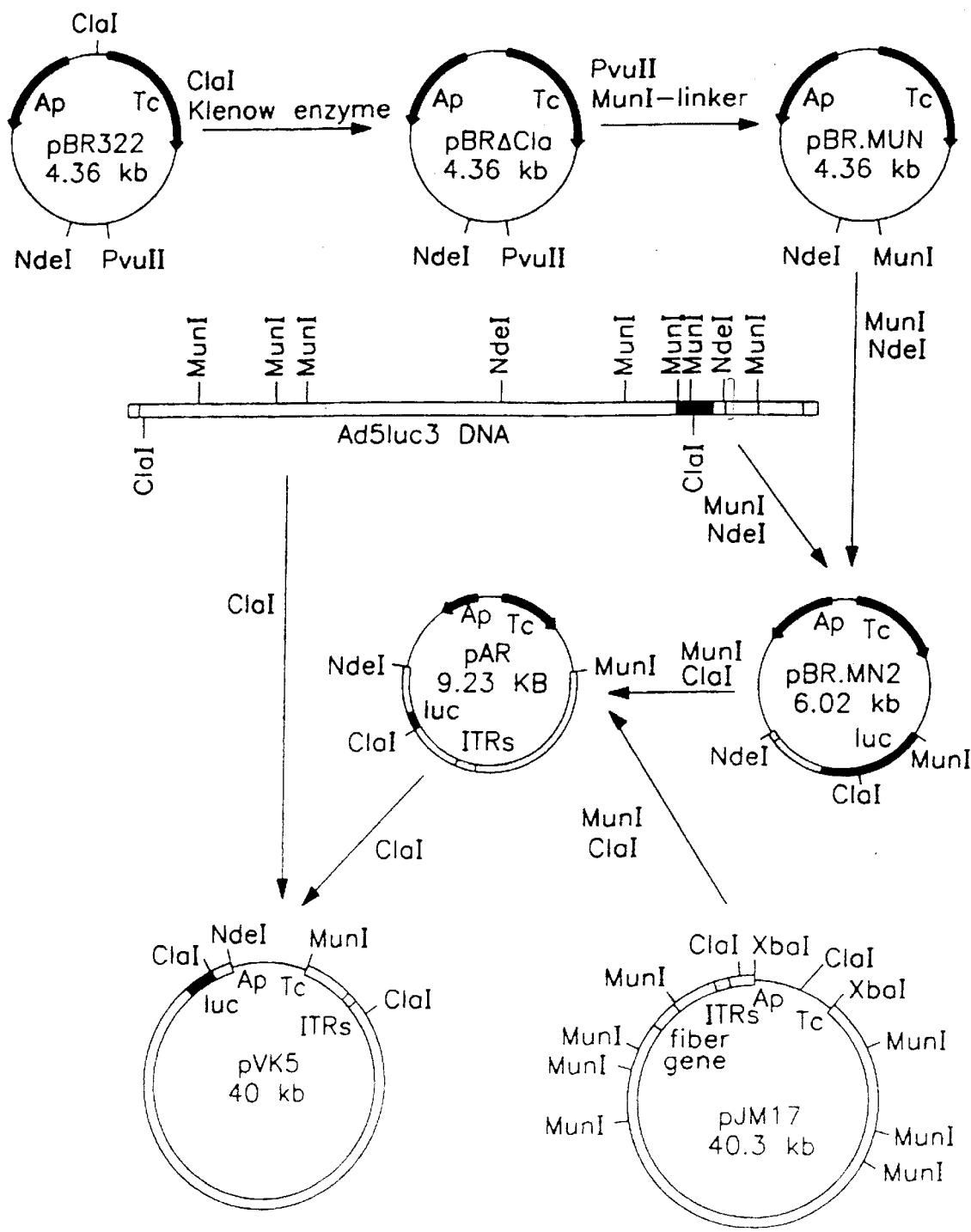
FIG. 8 shows the construction of a fiber rescue plasmid for generation of adenoviral vectors with fiber variants. The schema for construction of the fiber rescue plasmid pVK5 is depicted. This plasmid contains an adenoviral genome derived from the recombinant adenovirus Ad5luc3, although it is deleted for the fiber gene. The deleted fiber is replaced with a "stuffer" segment representing a bacterial plasmid backbone. The fiber defect prevents the generation of viable adenoviral progeny after transfection of mammalian cells with the rescue plasmid. Furthermore, its size exceeds the packaging constraints of the adenoviral capsid.

A fiber rescue plasmid was constructed for recombination with shuttle plasmids containing fiber variants. For this construction, the commercial plasmid pBR322 was modified to provide restriction sites of utility. First, the ClaI site was destroyed by linearization with ClaI, the termini were blunted by a Klenow enzyme fill-in reaction and the plasmid was re-circularized. The resultant plasmid, pBRΔCla, was then digested with PvuII and ligated with the MunI linker, 5' CCCCAATTGGGG 3' (SEQ ID NO. 1), resulting in the plasmid pBR.MUN, which served as the cloning vector for subsequent constructions. Three distinct segments comprising the adenoviral genome were then cloned into pBR.MUN. First, a 1.9 kb NdeI-MunI fragment from the genome of the recombinant adenovirus Ad5luc3 was excised. This recombinant adenovirus is a replication-competent vector containing the firefly luciferase gene in place of the deleted E3 region (25) and was provided by F. Graham (McMaster University, Hamilton, Ontario, Canada). The Ad5luc3 1.9 kb fragment was cloned into the corresponding sites of pBR.MUN to create the plasmid pRB.MN2. This plasmid contains a unique ClaI site within the luciferase segment of the cloned Ad5luc3 NdeI-MunI fragment. This ClaI site and a MunI site were then employed to clone a 4.0 kb ClaI-MunI DNA fragment from the plasmid pJM17 (26) containing the joined adenoviral inverted terminal repeats (ITRs). The plasmid pJM17 contains a full sized circularized adenoviral genome. Since the ClaI site of interest in pJM17 overlaps with Dam-methylation sites, to provide accessibility for ClaI digestion the plasmid was isolated from Dam-*Escherichia coli* strain JM110. The resultant plasmid, pAR, contains the pBR.MUN backbone flanked by two segments of adenoviral genomic DNA which normally flank the fiber gene in the Ad5luc3 genome. To complete the construction of the rescue plasmid, a 30 kb ClaI fragment from Ad5luc3 genomic DNA was cloned into the unique ClaI site of pAR. After electroporation of the ligated DNA into *E. coli* SURE cells (Stratagene, LaJolla, Calif.), ampicillin resistant clones were isolated for restriction analysis. The complete rescue plasmid was designated pVK5 as shown in FIG. 8.

Figure 9:
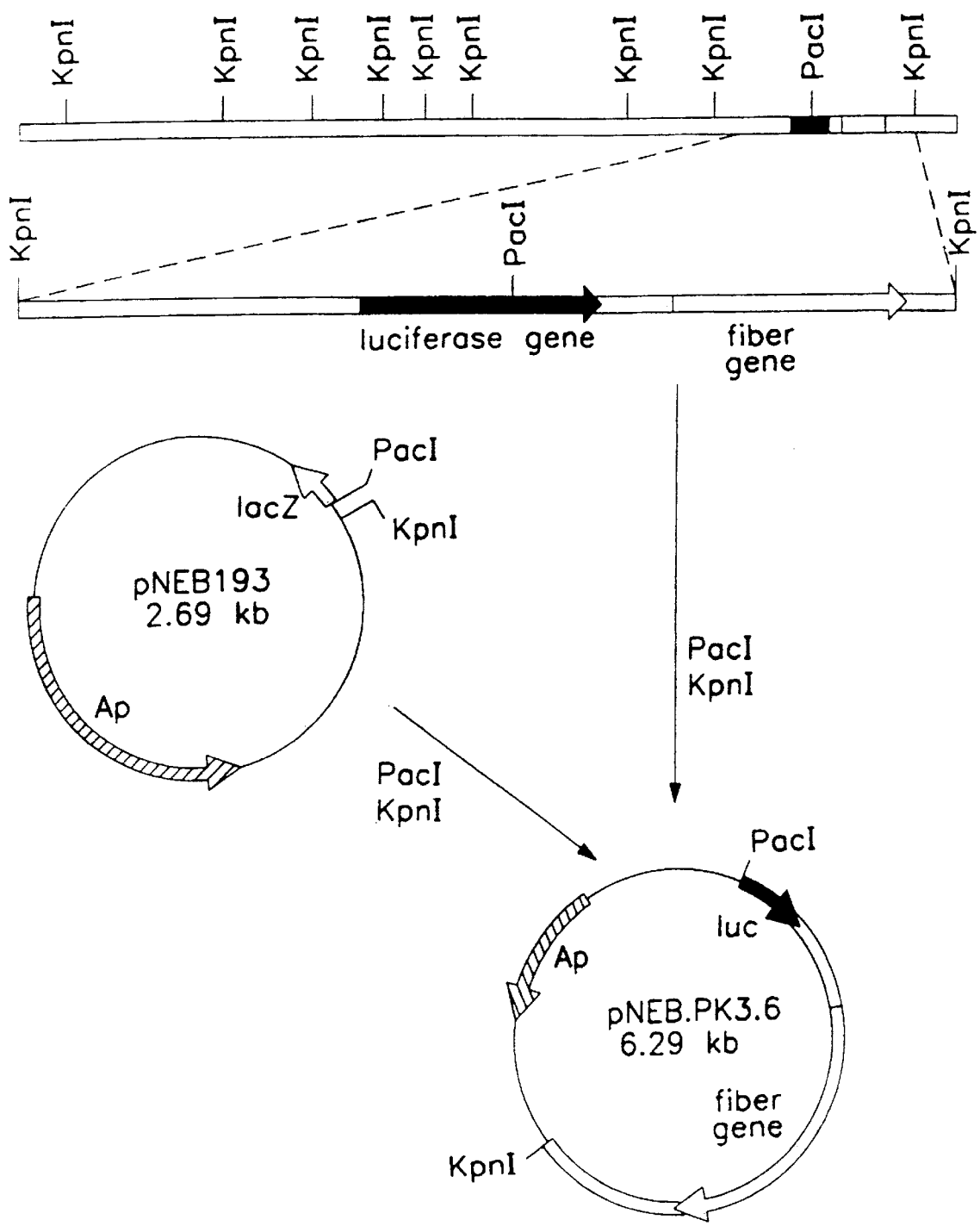
FIG. 9 shows the construction of a fiber shuttle plasmid for generation of adenoviral vectors with fiber variants. The schema for construction of the fiber shuttle plasmid pNEB.PK3.6 is depicted. This plasmid contains the adenoviral fiber gene plus flanking regions of the adenoviral genome.

A fiber shuttle plasmid was generated for incorporation of fiber variants into the adenoviral genome by recombination with the adenoviral fiber rescue plasmid pVK5. To construct the shuttle plasmid, a 3.6 kb PacI-KpnI DNA fragment of Ad5luc3 DNA was cloned into the corresponding sites of the commercial vector pNEB 193 (New England Biolabs, Cambridge, Mass.). The resulting plasmid, pNEB.PK3.6, contains a complete copy of the Ad5 fiber gene flanked by two segments of Ad5luc3 DNA of approximately 1.1 kb and 0.8 kb in length as shown in FIG. 9.

To facilitate genetic manipulation of the Ad5 fiber gene, a master plasmid pBS.F5wt was made as follows: plasmid pTF5F [24] was digested with Acc65.I, treated with Klenow enzyme, digested with MunI and ligated with EcoICRI-EcoRI-digested pBluescript KS II (Stratagene, La Jolla, Calif.). The resulting plasmid, pBS.F5wt, contains the full length fiber ORF followed by part of the 3' untranslated region of the gene. To engineer a gene suitable for the construction of fiber fusions, a unique FspI restriction site was introduced at the 3' end of the fiber ORF by PCR-based mutagenesis. Primers F5.F1, 5'-ATG AAG CGC GCC AGA CCG TCT GAA G-3' (SEQ ID NO. 2) and
F5.R1, 5'-TTA GAG CTC TTG GGC AAT GTA TGA AAA AGT G-3' (SEQ ID NO. 3), were used with pTF5F as a template to amplify the modified fiber gene. The PCR product was then digested with BglII and a 0.3 kb DNA fragment was cloned into BglII-EcoRV-digested pBS.F5wt resulting in pBS.F5.LEU. As a result of these modifications, the last GAA codon of the fiber ORF was mutated into GAG and CTC was added to the sequence. This resulted in a unique EcoICRI-restriction site at the 3'-end of the fiber gene. To facilitate the sub cloning of the chimeric fiber gene constructed in pBS.F5.LEU into the fiber shuttle vector pNEB.PK3.6, a segment of the 3' untranslated region of the fiber gene was synthesized as two oligonucleotides (5'-CTC TAA AGA ATC GTT TGT GTT ATG TTT CAA CGT GTT TAT TTT TCA ATT GAA GCT TAT-3'
(SEQ ID NO. 4) and
5'-CGA TAA GCT TCA ATT GAA AAA TAA ACA CGT TGA AAC ATA ACA CAA ACG ATT CTT TAG AG-3'
(SEQ ID NO. 5))

and cloned into EcoICRI-ClaI-digested pBS.F5.LEU. The resulting plasmid, pBS.F5.UTR, was then used for all subsequent modifications of the fiber gene.

To generate recombinant fiber genes encoding chimeric fibers consisting of the Ad5 fiber tail and shaft domains with knob domains derived from other adenoviruses, a plasmid pSHAFT was made as follows. Two PCR primers (5'-ATG CAC CAA ACA CAA ATC CCC TCA A-3' (SEQ ID NO. 6) and
5'-CTC TTT CCC GGG TTA GCT TAT CAT TAT TTT TG-3' (SEQ ID NO. 7))

were used to modify the sequence of the Ad5 fiber gene coding for the TLWT motif highly conserved in most characterized mammalian adenovirus fiber genes [42]. The DNA fragment generated with these primers from Ad5-Luc 3 genomic DNA was then digested with NcoI and cloned into NcoI-EcoICRI-digested pBS.F5.UTR. The plasmid pSHAFT contains a truncated sequence of the Ad5 fiber gene with an unique SmaI site located next to a Leu codon preceding the TLWT coding sequence. This plasmid was then used to construct a chimeric Ad5/Ad3 fiber gene. For this construction, a portion of the Ad3 fiber gene coding for the knob domain was PCR-amplified using plasmid pBR.Ad3Fib (provided by J. Chrobozcek, Grenoble, France), and a pair of primers:

5'-TAT GGA CAG GTC CAA AAC CAG AAG C-3' (SEQ ID NO. 8) and
5'-TTT ATT AGT CAT CTT CTC TAA TAT AGG AAA AGG-3' (SEQ ID NO. 9).

The PCR product was then cloned into SmaI-EcoICRI-digested pSHAFT, resulting in pBS.F5/3, which contains a chimeric fiber gene coding for the tail and shaft domains of Ad5 and the knob domain of Ad3 fiber. To subclone the recombinant fiber gene into the fiber shuttle vector, a 0.73 kb NcoI-MunI DNA fragment of pBS.F5/3 was cloned into NcoI-MunI-digested pNEB.PK3.6, resulting in pNEB.PK.F5/3.

EXAMPLE 9
Mutagenesis of adenoviral fiber gene

To create a silent mutation in the adenoviral fiber gene, a polymerase chain reaction (PCR)-based mutagenesis method was employed to modify codon Ala-579 of the fiber open reading frame (ORF) from GCC to GCG. This substitution at position 1737 of the fiber open reading frame creates a novel recognition site for the restriction endonuclease FspI. Two pairs of primers were designed for this mutagenesis:

primer F1 = 5' AAC AAA ATG TGG CAG TCA AAT AC 3' (SEQ ID NO. 10), primer F2 = 5' CAT ACA TTG CGC AAG AAT AAA G 3' (SEQ ID NO. 11), primer R1 = 5' CTT TAT TCT TGC GCA ATG TAT G 3' (SEQ ID NO. 12), and primer R2 = 5' TGA TGC ACG ATT ATG ACT CTA CC 3' (SEQ ID NO. 13).

Figure 10:
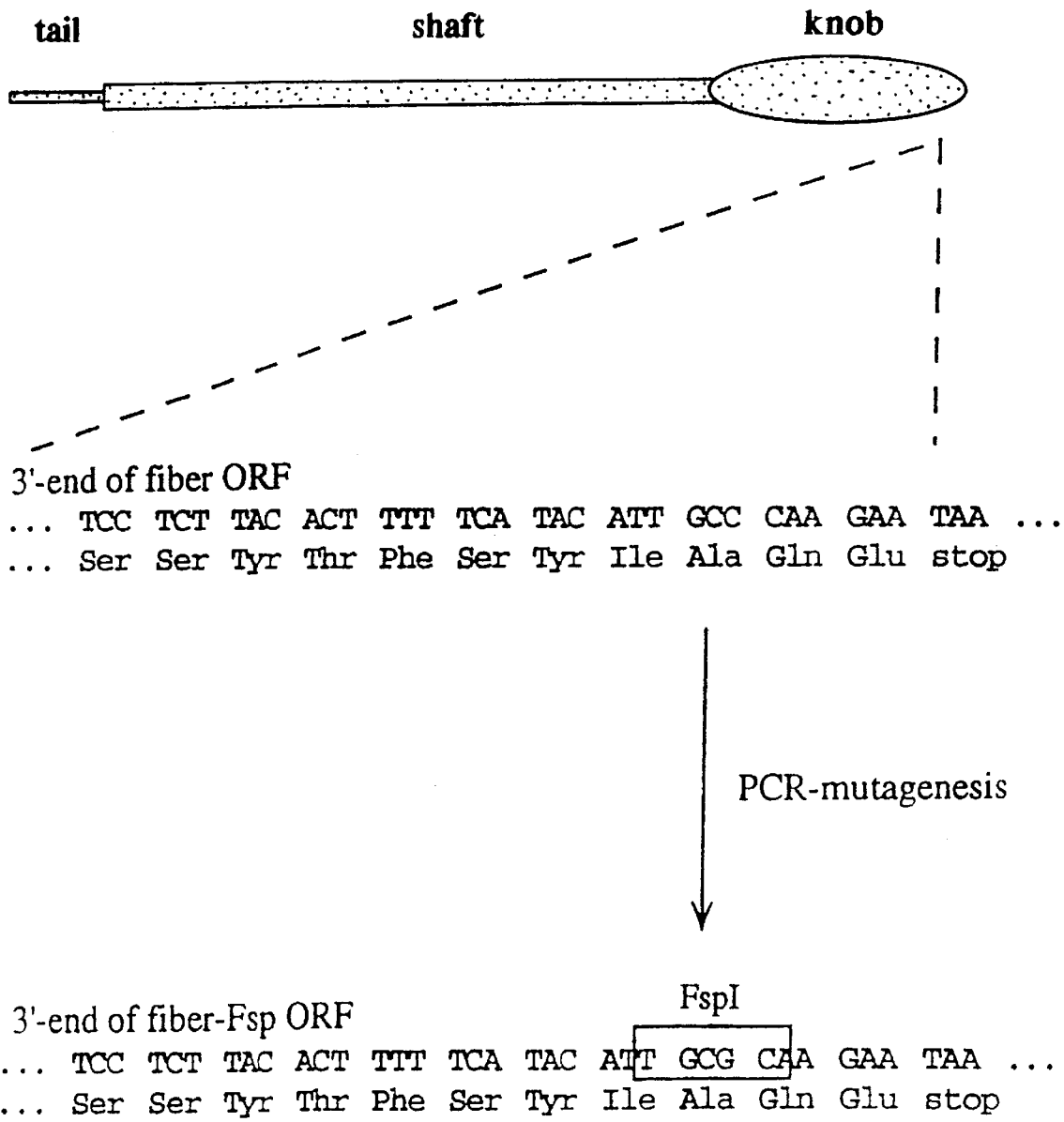
FIG. 10 shows the construction of a mutant fiber gene containing a functionally silent mutation. The 3' end of the fiber gene corresponds to the knob domain of the fiber protein. PCR-mutagenesis was employed to generate a single base substitution (C to G) which creates a silent mutation resulting in a novel recognition site for the restriction endonuclease FspI.

Primers F2 and R1 are complementary to the site of the mutation; primers F1 and R2 are complementary to DNA sequences outside the mutation site and designed as partners for R1 and F2, correspondingly. Generation of the mutation was accomplished via two sequential PCR reactions. First, primers F1-R1 and F2-R2 were used with pNEB.PK3.6 to generate two DNA fragments overlapping at the mutation site. These two fragments were then employed as a template for a second PCR with primers F1-R2. The DNA fragment generated via the second PCR reaction contained the mutated alanine codon (see FIG. 10). To transfer the mutated segment of the fiber gene into pNEB.PK3.6, the PCR product was digested with BstXI and MunI. The 0.36 kb fragment generated was used to replace the analogous segment in pNEB.PK3.6. The DNA of the new plasmid, pNEB.PK.FSP, was partially sequenced to confirm the presence of the mutation.

EXAMPLE 10
Generation of recombinant adenovirus with a modified fiber gene

Figure 11:
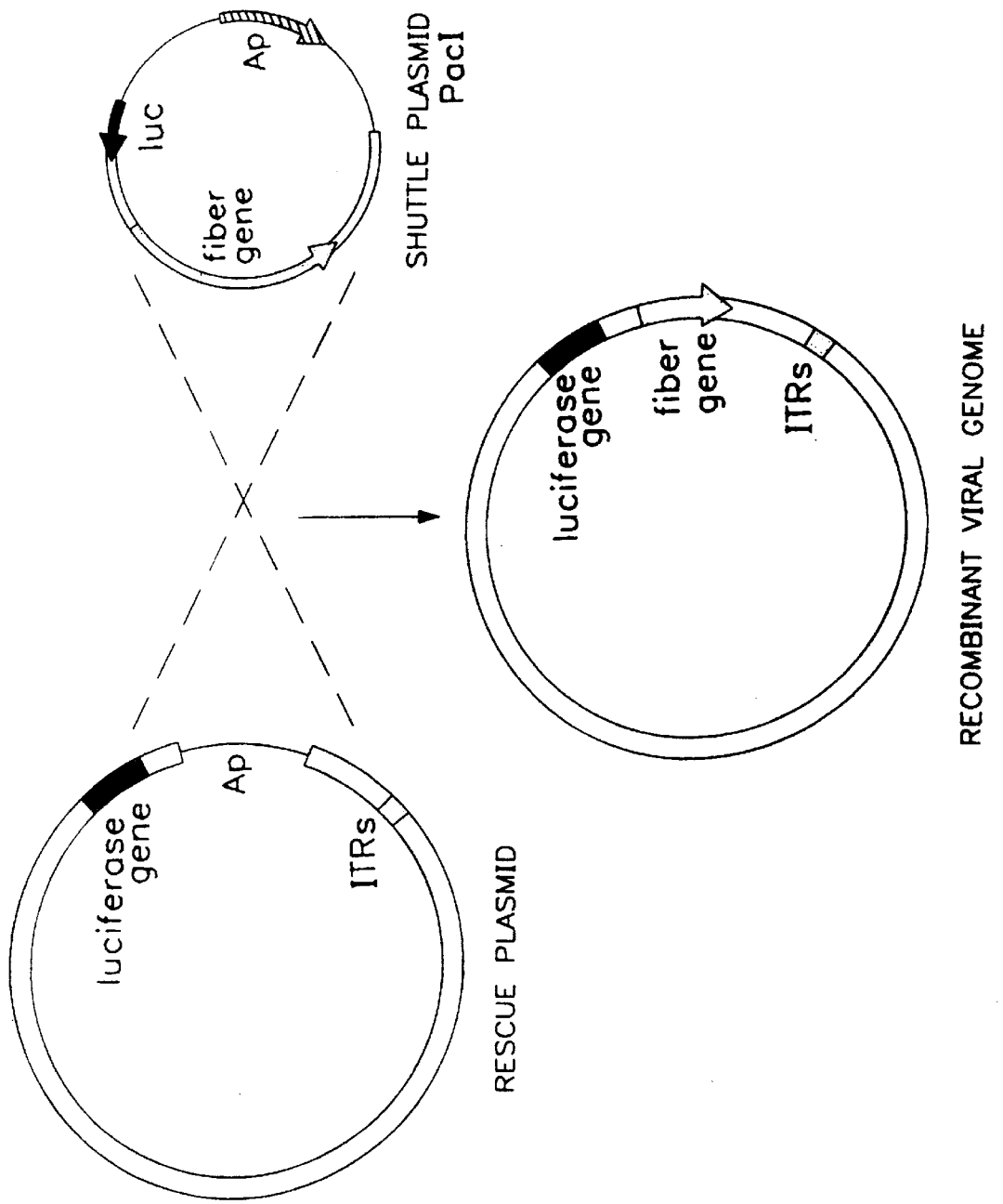
FIG. 11 shows the schema for generation of an adenoviral vector containing fiber variants employing in vivo homologous recombination. Recombination between the fiber rescue plasmid, pVK5, and the shuttle plasmid, pNEB.PK.FSP, would be predicted to yield the depicted recombinant adenoviral genome. This recombinant genome would contain the fiber variant gene originating from the shuttle plasmid.

After validation of the presence of the silent fiber mutation, the mutated segment of the fiber gene was incorporated into the pNEB.PK3.6 fiber shuttle vector. To construct recombinant adenovirus containing the mutated fiber gene, the newly generated fiber shuttle plasmid, pNEB.PK.FSP, and the rescue plasmid, pVK5, were co-transfected into 293 cells. The schema for the predicted recombination event is shown in FIG. 11. In this strategy, recombination between homologous regions of the two plasmids would be predicted to yield an intact viral genome whereby the fiber defect in the rescue plasmid was rectified. Such a genome would be capable of generating progeny virions as evidenced by plaque formation. To be successful in generating progeny virus, the recombination event would thus require excision of the oversized "stuffer" segment in the deleted fiber region, as well as incorporation of an intact, functional fiber into the rescue plasmid.

Figure 12A:
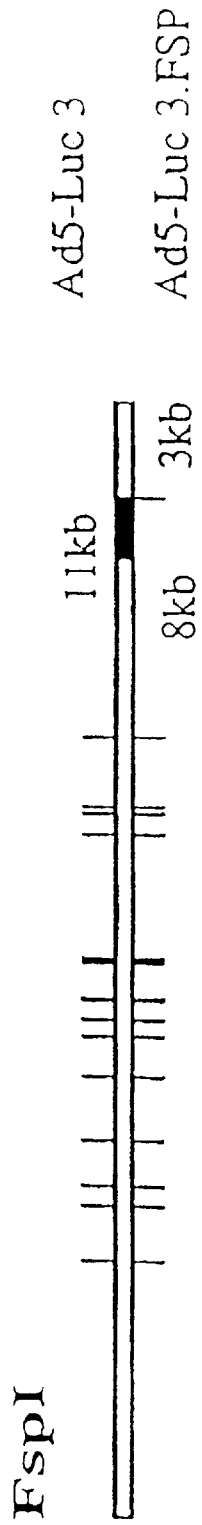
FIGS. 12A–12B show the analysis of recombinant adenovirus containing fiber variant generated by two plasmid system.
Figure 12B:
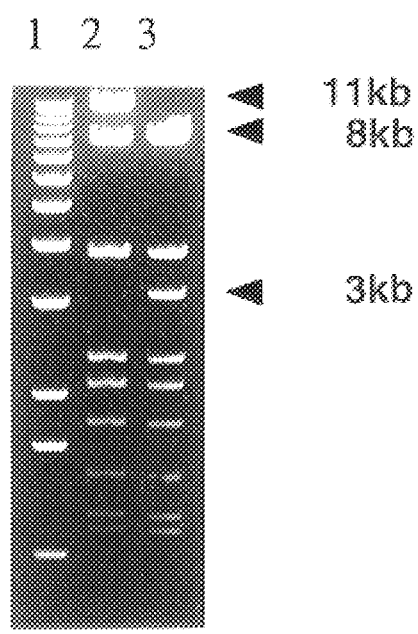
Figure 13:
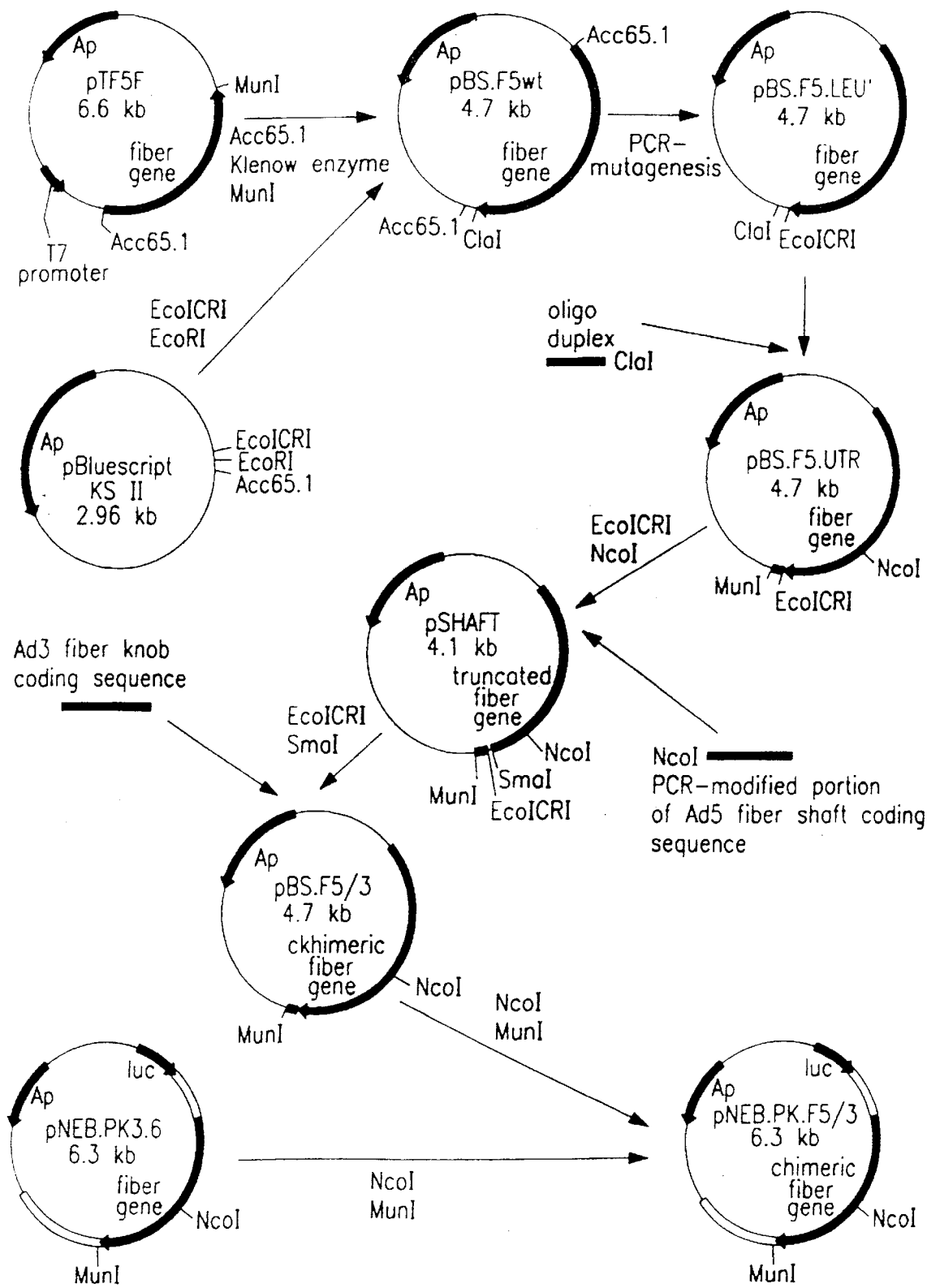
FIG. 13 shows the schema for construction of the plasmid, pNEB.PK.F5/3, which contains a chimeric fiber gene encoding the tail and shaft domains of Ad5 and the knob of Ad3.
Figure 14A:
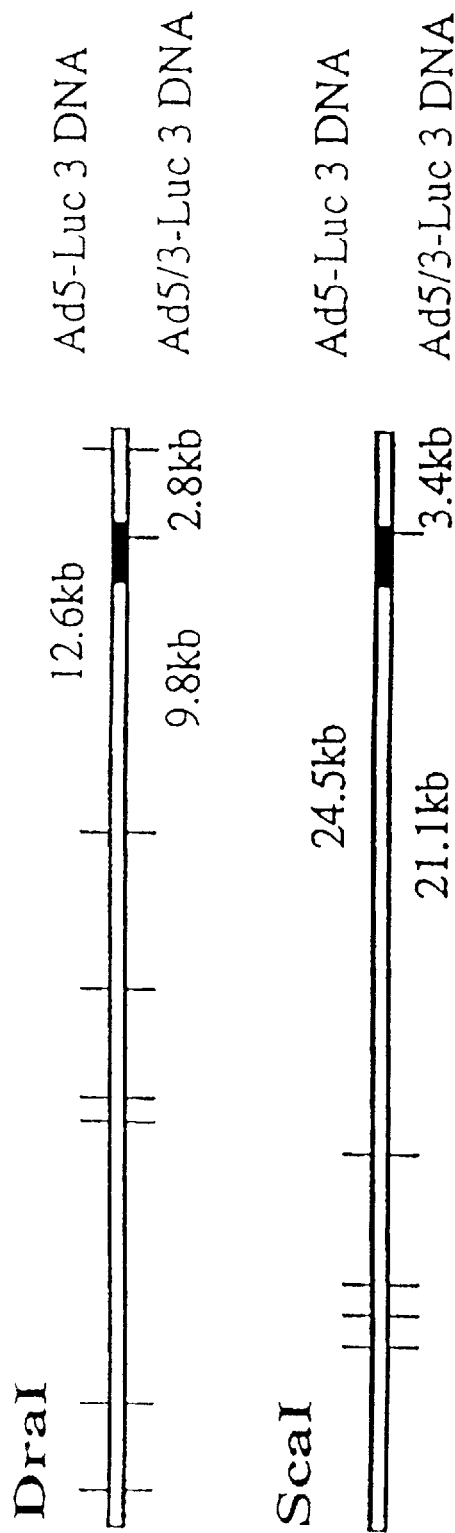
FIGS. 14A–14B show an analysis of recombinant adenovirus containing chimeric fibers.
Figure 14B:
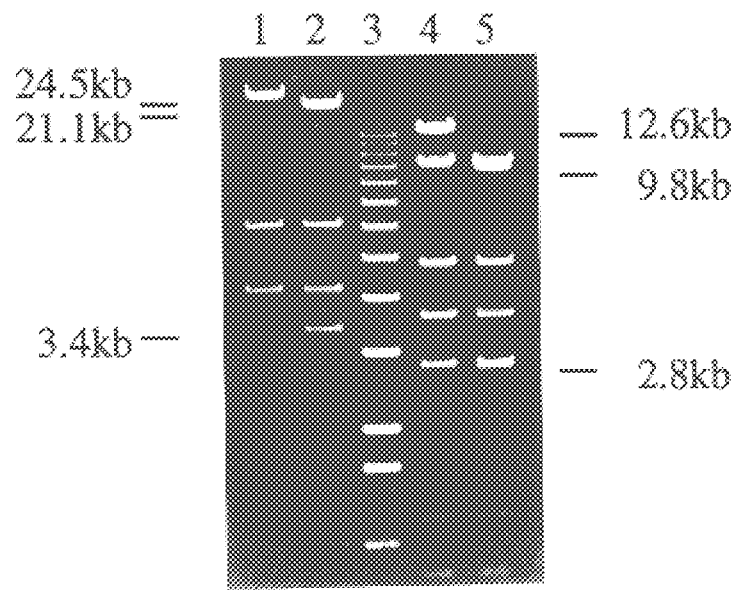

After initial transfection of 293 cells with the two plasmid system, CPE was noted in the infected cells, indicating the presence of infectious viral progeny. Control transfections with only pVK5 or only pNEB.PK.FSP did not yield CPE, confirming that the component plasmids were not individually capable of directing viral progeny synthesis. Cells from co-transfected plates with evidence of viral propagation were lysed to release virus which was then expanded to permit genomic analysis. Viral DNA was subjected to restriction endonuclease analysis with FspI to confirm the presence of the silent fiber mutation. The pattern of this digestion corresponded to the pattern predicted by virtue of incorporation of the mutated fiber gene (FIG. 12A). In this regard, an 11 kb fragment is noted in Ad5luc3 genomic DNA digested by FspI, corresponding to the right terminus of the viral genome (FIG. 12B). In contrast, in the viral DNA isolated from the co-transfected cells, FspI digestion yielded DNA fragments of 8 and 3 kb. This pattern is predicted based upon the introduction of the additional FspI site into the progeny virus by virtue of a recombinational event between the fiber shuttle and rescue plasmids. These findings are consistent with the concept that an in vivo recombinational event has resulted in the derivation of a recombinant adenovirus incorporating the modified fiber protein.

The design of the two plasmid rescue systems included an incorporated luciferase reporter gene for monitoring the efficacy of the in vivo homologous recombinational event. In this regard, the firefly luciferase reporter gene was originally placed in the context of a deleted E3 domain in the replication-competent recombinant adenovirus Ad5luc3 (25). In the two plasmid rescue system, the proximity of the luciferase open reading frame to the 5' fiber flanking regions would predict its involvement in at least a subset of productive recombinational events. In this regard, progeny virions have demonstrated the capacity to accomplish efficient transfer of luciferase activity to heterologous cells, as has been noted with the parent vector (data not shown). Thus, the incorporation of this reporter gene provided an additional method of validating the fidelity of the recombinational events allowing progeny virus derivation.

The present invention facilitates analysis of key parameters relating to the biology of adenoviral capsid assembly. Thus, one can now determine structural modifications of the fiber protein which are compatible with the ability of fiber to assume its native configuration for assembly of mature particles based upon association with penton base capsomers (32). In addition, the development of the described fiber rescue system permits the derivation of adenoviral vectors containing modified fiber proteins. This step is of key utility in the context of strategies to develop tropism-modified adenoviruses capable of targeted, cell-specific gene delivery. In this regard, genetic methods have been successfully employed to alter the tropism of retroviral vectors towards the goal of cell-specific targeting (34). This has been accomplished both by pseudotyping (35), as well as by direct genetic modifications of the envelope glycoprotein of the retroviral particle (36). In the latter instance, cell specific targeting has been achieved employing ligands or single-chain antibodies in fusion with the envelope glycoprotein as targeting moieties. Thus, a substantial body of work has validated the concept of tropism-modification of retroviral vectors as a means to achieve targeted, cell-specific gene delivery (34).

Despite these advancements in retroviral vector development, the direct utility of this maneuver with regards to practical gene therapy approaches is not immediately apparent. This derives from the fact that retroviruses are highly labile in vivo (37). This phenomenon is understood to reflect effective humoral-mediated clearance subsequent to intravascular delivery. It must therefore be recognized that the various targeting maneuvers are not of a high level of utility in the context of strategies designed to accomplish direct, in vivo transduction subsequent to systemic administration. Thus, despite the acquisition of a targeting capacity, these modifications have not allowed a more generalized use of retroviral vectors for transduction of non-localized targets. In contrast, adenoviruses are highly competent in achieving direct in vivo gene delivery (4,19). Thus, modifications to adenoviral vectors allowing cell-specific targeting would appear to be of direct utility in gene therapy approaches. To this end, strategies have been pursued to achieve modification of the native binding domain of the adenovirus as a means to alter parent virus tropism. The present invention developed the methods required to incorporate these fiber-ligand chimeras into particles for derivation of tropism-modified virions.

In the present invention, the feasibility of using a two plasmid rescue system for deriving adenoviral vectors containing fiber gene variants was demonstrated. This strategy was undertaken to produce a rapid and facile method for the derivation of these agents. In this regard, direct cloning in the context of the large (36 kb) and complex adenoviral genome is limited by its technical complexity. In addition, whereas adenoviral pseudotypes have been derived (38), their utility for cell-specific targeting purposes would be limited, as many of the various adenoviral serotypes are characterized by the broad tropism profiles of the major human fiber serotypes (39). Thus, a strategy of direct genetic modification of the fiber gene as a means to achieve specific alteration of viral tropism has been developed. The present invention demonstrates that variant fiber molecules can be incorporated into mature particles. A person having ordinary skill in this art would therefore be able to incorporate fiber variants with targeting potential in mature particles employing these same methods.

EXAMPLE 11

Construction of a two-plasmid rescue system for derivation of adenoviral fiber recombinants Methods were developed to produce recombinant adenoviral vectors employing in vivo homologous recombination. These methods are based upon non-infectious adenoviral genome constructs undergoing recombination in target cells to yield an infectious viral genome capable of propagation of progeny virions. Techniques reported to date have included the use of overlapping linear DNA constructs (29–31), as well as the use of plasmid based systems (26). In the latter instance, a two plasmid strategy based upon recombination between a "shuttle plasmid", containing heterologous sequences, and a "rescue plasmid", providing the required viral functions, has been widely employed (26).

The latter methodology was employed for the strategy to generate adenoviral fiber variants of the present invention. As a first step towards this goal, the fiber rescue plasmid, pVK5, was constructed for recombination with fiber variant containing constructs (FIG. 8). This plasmid, pVK5, was designed to possess the key attributes of described rescue plasmid vectors. The fiber rescue plasmid contains a viral genome joined at the ITRs within a prokaryotic vector backbone. The adenoviral genome is deleted for the fiber gene via substitution with a bacterial plasmid segment. In addition, the prokaryotic vector backbone "stuffer" segment results in an oversized, and thus unpackagable, adenoviral genome. Thus, the plasmid pVK5 would not be capable of generating progeny virions after transfection into eucaryotic cells, due to its size, in addition to the fact that viral fiber functions are of essential importance (32, 33) for lateral infection and thus progeny plaque generation.

The derived rescue plasmid differs in several additional respects from described adenoviral plasmid recombination systems (27–31). In this construction, the adenoviral E1A/B regions were retained to allow replication of derived recombinant adenoviruses in a variety of cellular targets. Deletion of this region could be accomplished, however, with the mandate that viral rescue procedures be carried out in the context of an E1-transcomplementing cell line, such as 293 (27). In addition, incorporated within the viral genome of the rescue plasmid is a luciferase reporter gene. To accomplish this, DNA segments derived from the recombinant adenovirus Ad5luc3 (25) which contains a firefly luciferase reporter gene in place of the deleted E3 region were utilized. The luciferase gene was included to provide an additional means of monitoring progeny viral competence within the context of the recombinational system of the present invention.

For employ with the fiber rescue plasmid pVK5, a fiber shuttle plasmid was also derived. This plasmid was designed to provide a complete copy of the fiber gene for generation of recombinant viral genome. To achieve efficient recombination with the rescue plasmid, the shuttle vector must contain flanking regions of viral DNA homologous to corresponding regions in the rescue plasmid. The lengths of these flanks require sufficient overlap to provide efficient in vivo homologous recombination between the two plasmids. The fiber shuttle vector pNEB.PK3.6 was thus designed to provide these functional requirements (FIG. 9). In addition, pNEB.PK3.6 contains several unique restriction sites convenient for making modifications of the fiber gene.

EXAMPLE 12

Cells 293 cells [27] were obtained from Microbix (Toronto, Canada) and maintained in Dulbecco's modified Eagle's medium/Ham's F12 (DMEM/F12) supplemented with 10% fetal calf serum (FCS) at 37° C. and 5% $CO_2$.

EXAMPLE 13

Expression of Ad5 and Ad3 knobs in *E. coli*

Recombinant adenovirus containing chimeric Ad5/Ad3 fibers was generated by in vitro recombination between pVK5 and pNEB.PK.F5/3 using methods described above. To confirm the identity of the rescued virus, its DNA was characterized by restriction digestion with DraI and ScaI.

The knob domains of Ad5 and Ad3 fibers were expressed in *E. coli* with N-terminal 6xHis tags using the pQE30 expression vector (Qiagen, Hilden, Germany). Ad5-Luc 3 DNA and plasmid pBR.Ad3Fib were used as templates for PCR to amplify the knob domains of the respective fiber genes. Primers for these reactions were:

F5.F, 5'-TTT AAG GAT TCC GGT GCC ATT ACA GTA GGA A-3' (SEQ ID NO. 14);
F5.R, 5'-TAT ATA AGC TTA TTC TTG GGC AAT GTA TGA-3' (SEQ ID NO. 15);
F3.F, 5'-CTC GGA TCC AAT TCT ATT GCA CTG AAA AAT AAC-3' (SEQ ID NO. 16); and
F3.R, 5'-GGG AAG CTT AGT CAT CTT CTC TAA TAT AGG AAA AGG-3' (SEQ ID NO. 17).

Each pair of primers amplified a DNA sequence coding for the knob domain plus the last repeat of the shaft domain of the corresponding fiber polypeptide. Both PCR products were then digested with BamHI and HindIII and cloned into BamHI-HindIII-digested pQE30, resulting in plasmids pQE.KNOB$_5$ and pQE.KNOB$_3$. Recombinant proteins isolated from *E. coli* M15(pREP4) cells harboring pQE-.KNOB$_5$ and pQE.KNOB$_3$ were purified on Ni-NTA agarose columns (Qiagen, Hilden, Germany). The ability of both proteins to form homotrimers was verified by SDS-PAGE of boiled and unboiled samples as described before [24, 55]. The concentrations of the purified knobs were determined by the Bradford protein assay (Bio Rad, Hercules, Calif.) using bovine IgG as the standard.

EXAMPLE 14

In vitro gene transfer mediated by the recombinant adenovirus containing chimeric fiber protein The construction of the adenoviral vector containing the chimeric fiber protein was undertaken to alter receptor tropism for purposes of targeted gene delivery. In this regard, adenovirus serotypes 3 and 5 achieve cellular entry via distinct cell surface receptors [22, 39]. Thus, to validate the functional utility of constructing the chimeric fiber, that entry of Ad5/3-Luc 3 occurred via the pathway dictated by the knob domain of the fiber was demonstrated. As the receptors for type 3 and type 5 adenoviruses coexist on many types of cells, including 293 cells, it was necessary to be able to validate specific entry via each pathway. Recombinant serotype 3 and 5 knobs were expressed in *E. coli* and SDS-polyacrylamide gel electrophoresis confirmed that the purified proteins were trimeric (data not shown). Various concentrations of each recombinant knob were preincubated with 293 cell monolayers prior to infection with the parent adenoviral vector Ad5-Luc 3 or the modified adenovirus Ad5/3-Luc 3. Since both viruses carry the gene encoding firefly luciferase, viral infectivity was measured indirectly by determination of luciferase activity in the infected cells. Thus, entry via the adenovirus type 5 receptor was confirmed employing competition with the recombinant type 5 knob and entry via the adenovirus type 3 receptor was confirmed by competition with the type 3 knob.

Figure 15A:
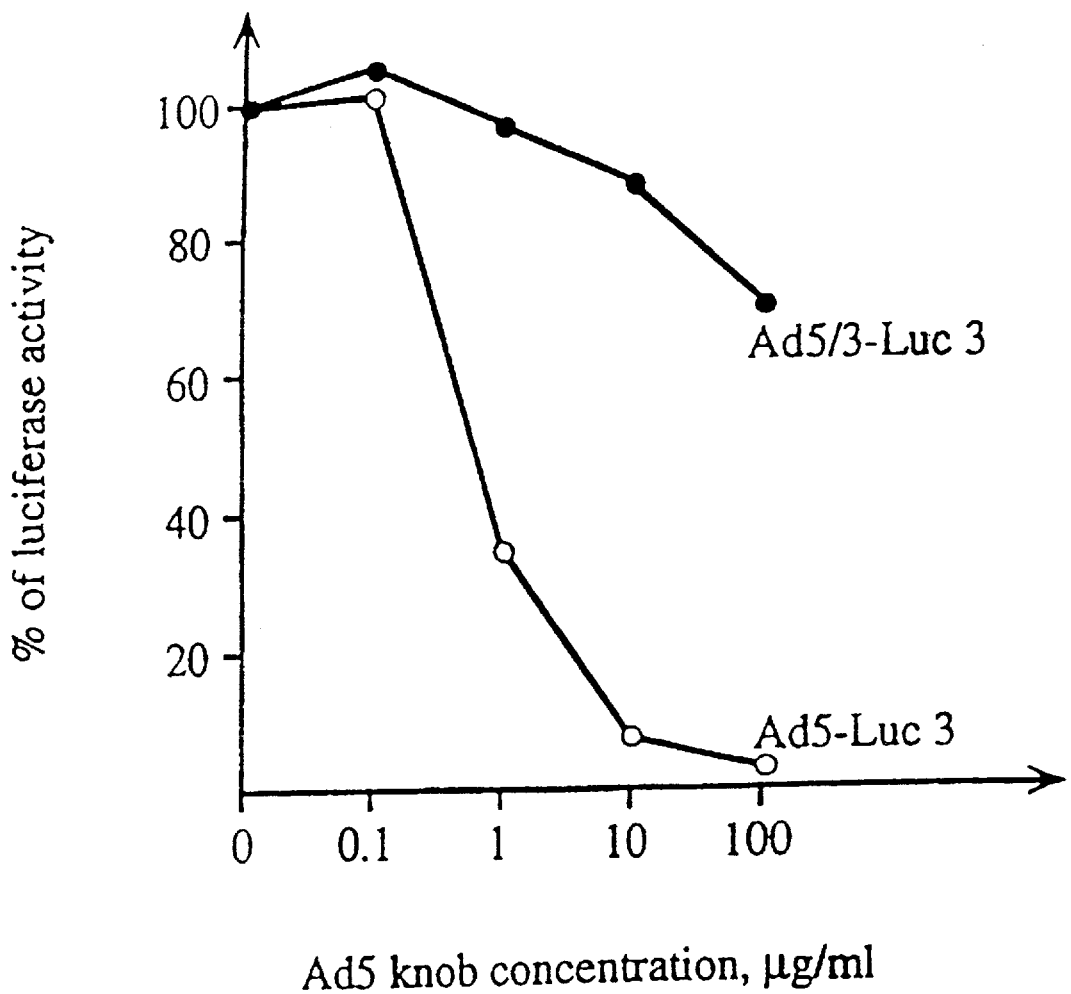
FIGS. 15A–15B show the type-specific inhibition of adenovirus infectivity by recombinant knobs. 293 cells were preincubated with either type 5 (FIG. 15A) or type 3 (FIG. 15B) knob at the indicated concentrations for 10 minutes at room temperature to allow receptor binding. Ad5-Luc 3 or Ad5/3-Luc 3 were then added at a multiplicity of infection of 10 and incubation was continued for another 30 minutes at room temperature. The viruses were aspirated and complete medium was added before transferring the cells to 37° C. After 30 hours, the cells were lysed and luciferase activity was determined. Luciferase activity is given as a percentage of the activity in the absence of blocking by recombinant knob. Points represent the mean of two determinations.
Figure 15B:
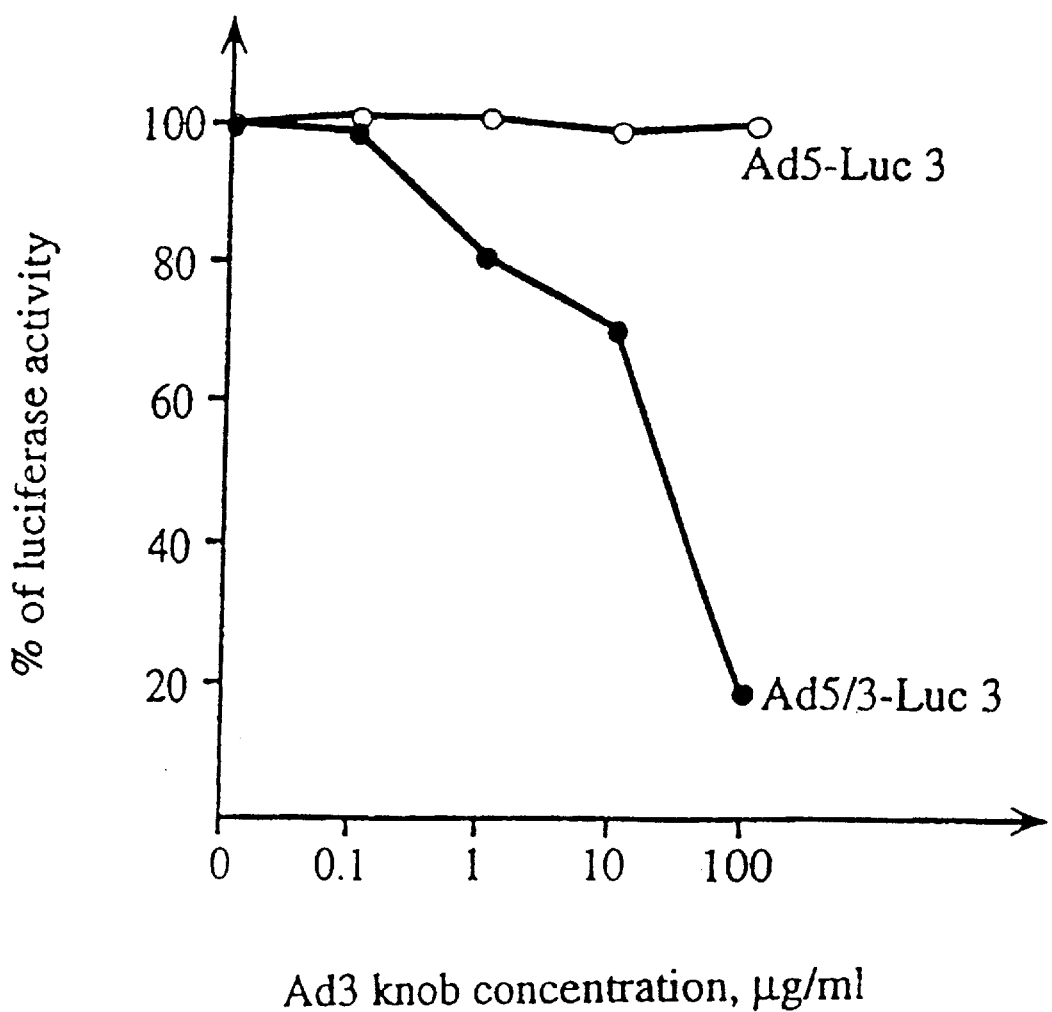

This analysis confirmed that competition with the recombinant type 5 knob inhibited the infectivity of the parent virus Ad5-Luc 3 in a dose-dependent manner. When employed at a concentration of 100 μg/ml, the type 5 knob inhibited 97% of the maximal luciferase activity, confirming that specific entry was via the adenovirus type 5 cellular receptor (FIG. 15A). The specificity of this interaction was confirmed in that type 3 fiber knob was not capable of blocking the gene transfer by Ad5-Luc 3 in competition experiments (FIG. 15B). A similar analysis was then carried out employing the Ad5/3-Luc 3 chimeric virus. In competition experiments employing the type 3 knob, it was observed that the Ad5/3-Luc 3-mediated gene transfer could be blocked in a dose-dependent manner. At a concentration of 100 μg/ml, the type 3 knob inhibited 80% of the maximal luciferase activity of Ad5/3-Luc 3 (FIG. 15B). Conversely, gene transfer by this modified virus was only minimally inhibited by high concentrations of type 5 knob (FIG. 15A). These findings thus confirm that Ad5/3-Luc 3, which contains a chimeric fiber protein with the knob domain derived from serotype 3, achieved cellular entry via the adenovirus type 3 pathway. Thus, the overall specificity of viral entry was dictated exclusively by the knob domain of the chimeric fiber.

EXAMPLE 15

To restrict gene delivery exclusively to the target cells, it is necessary to prevent the interaction between the knob domain of the adenovirus fiber and its cellular receptor which plays the major role in the determination of adenoviral tropism. Since the specific amino acid residues in the knob which recognize the cell surface receptor have not yet been identified, it is not currently possible to ablate this binding site by employing genetic techniques such as site-directed mutagenesis. However, a neutralizing anti-knob antibody would be capable of blocking the primary interaction between the adenovirus fiber and its cognate cellular receptor. The present invention shows that if such an antibody were chemically conjugated to a ligand recognizing a specific cell surface receptor, it targets the adenoviral vector to this novel receptor.

The first stage in developing the targeted adenoviral vector of this embodiment of the present invention was therefore the generation of a neutralizing anti-knob monoclonal antibody (mAb). Hybridomas were generated by standard techniques after immunization of mice with intact Ad5 followed by two rounds of immunization with purified recombinant Ad5 knob. Supernatants from these hybridomas were assayed for the phenotypic characteristics important in modifying adenoviral tropism via immunological crosslinking: (i) reactivity with trimeric recombinant Ad5 knob, as determined in an ELISA; and (ii) inhibition of Ad5 infection of HeLa cells, as determined by neutralization of adenoviral cytopathic effect (CPE). On the basis of its high affinity binding to recombinant Ad5 knob and its ability to neutralize Ad5 infection of HeLa cells (data not shown), one clone, designated 1D6.14, was chosen for examination and the mAb was purified from ascites fluid by affinity chromatography using an immobilized protein A column.

Figure 16:
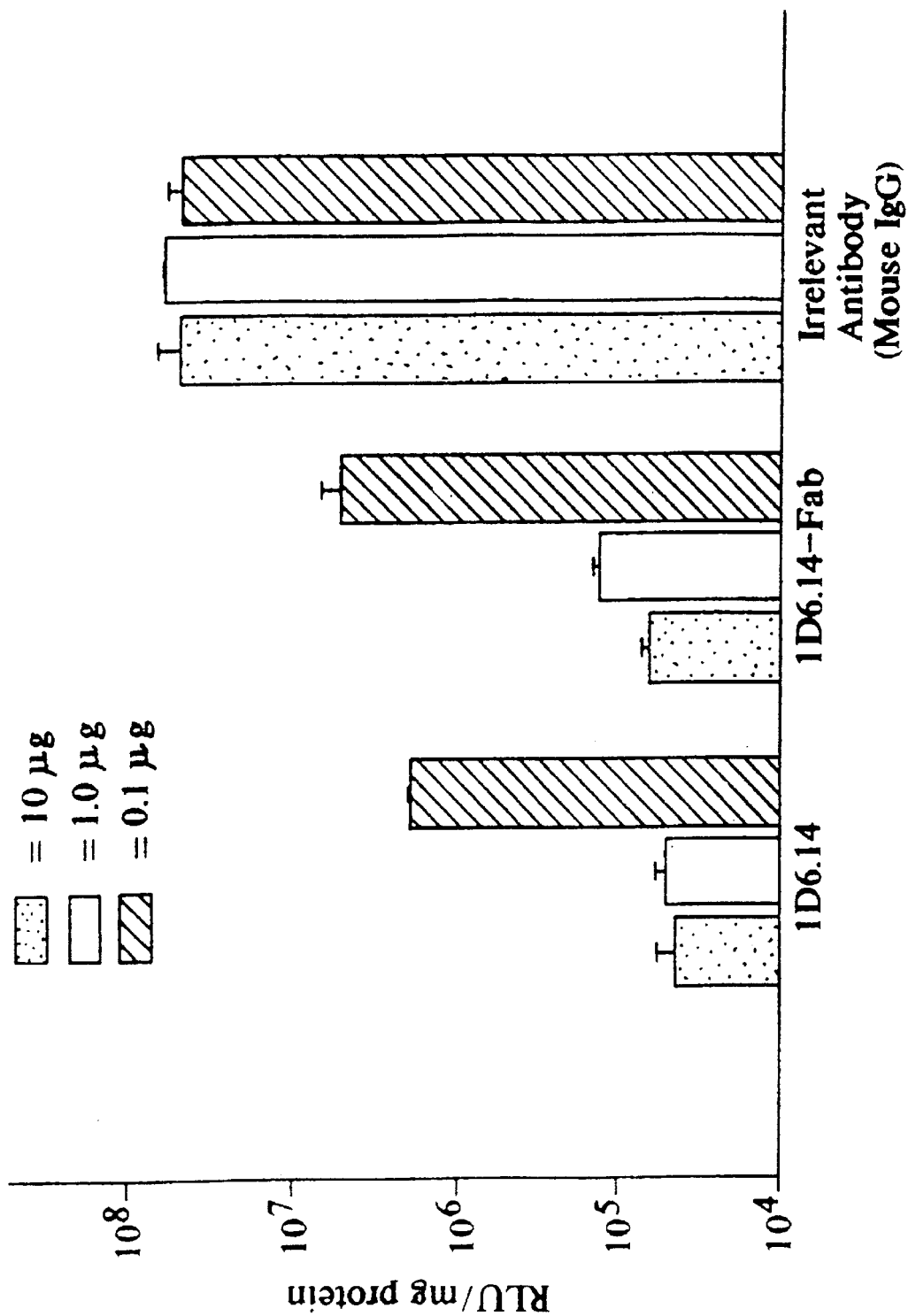
FIG. 16 shows that the anti-knob mAb 1D6.14 and its Fab fragment neutralize adenoviral infection. Anti-knob mAbs were generated after immunization of BALB/c mice with Ad5, followed by two rounds of immunization with recombinant Ad5knob (Henry, et al., J. Virol. 68, 5239–5246 (1994). On the basis of its high affinity binding to recombinant Ad5 knob in an ELISA and its ability to neutralize Ad5 infection of HeLa cells as determined in an endpoint CPE assay, one clone, designated 1D6.14, was chosen for further study. This mAb was purified using an ImmunoPure IgG purification kit (Pierce). Fab fragments were purified from intact 1D6.14 using an ImmunoPure Fab purification kit (Pierce). After dialysis against PBS, the concentrations of the purified mAb and Fab fragments were determined using the Bio-Rad protein assay. Varying dilutions of intact anti-knob mAb 1D6.14, the Fab fragment or an irrelevant antibody (mouse IgG) were incubated at room temperature in a total volume of 20 ml HBS with $10^8$ particles of AdCMVLuc, an adenoviral vector which expresses firefly luciferase from the CMV promoter. The expression of luciferase activity in cells infected with this vector is directly proportional to the number of infecting virus particles. After 30 minutes, the volume was increased to 1 ml with DMEM/ F-12±2% FCS and the complexes were added to 6-well plates containing 80% confluent HeLa cell monolayers previously rinsed with PBS. After incubation for 24 hours at 37° C., the cells were lysed and extracts assayed for luciferase activity using a luciferase assay system (Promega). The protein concentration of the lysates was determined to permit normalization of the data, which are expressed as relative light units per mg of cellular protein. Results are the mean of triplicate experiments.

To develop a targeted adenoviral vector by immunological methods, it was preferable to employ the Fab fragment of the antibody rather than the intact immunoglobulin. In this manner, the two antigen-binding arms of the parent antibody was prevented from crosslinking different viruses to form large complexes which might prove refractory to cellular uptake. Therefore, intact 1D6.14 was digested with papain and the Fab fragments were purified. As shown in FIG. 16, both the parent antibody and the Fab fragment were capable of neutralizing adenovirus infection in a dose-dependent manner, whereas an irrelevant control antibody failed to block infection.

Next, the ability to recognize specific receptors expressed on the surface of the target cells was introduced. A conjugate of the vitamin folate and the Fab fragment of the neutralizing anti-knob mAb was constructed. This was done with the aim of targeting adenoviruses to the high affinity folate receptor ($K_d$ $10^{-9}$M), which is overexpressed on the surface of several malignant cell lines, including ovarian, lung and breast carcinomas and brain tumors. Folate can be conjugated via its γ-carboxylate group to a variety of macromolecules, including antibodies, without losing affinity for its cellular receptor. Since folate and folate-macromolecule conjugates are internalized via the folate receptor by a mechanism termed potocytosis which involves nonclathrin-coated caveolae with a diameter of 60 nm, an adenovirus (diameter 65–80 nm, excluding the fibers) would be too large to enter this pathway. However, after binding specifically to the cell surface folate receptors, the adenoviral vector was able to accomplish internalization by its native endocytotic pathway mediated by the interaction of the penton base with secondary host cell receptors, av integrins.

Carboxyl groups of folate were coupled to amine groups of the Fab fragment of anti-knob mAb 1D6.14 by a carbodiimide procedure, as described by Kranz, et al., *Proc. Natl. Acad. Sci. USA* 92, 9057–9061 (1995). The resulting conjugate, hereafter referred to as the Fab-folate conjugate, was characterized both structurally and functionally. The conjugation of folate to the antibody fragment was verified by SDS-PAGE under denaturing conditions followed by immunoblot analysis employing an anti-folate mAb. An alkaline phosphatase-conjugated secondary antibody specific for the Fc region of mouse IgG was used to prevent cross-reaction with the Fab fragment of 1D6.14. The anti-folate antibody reacted specifically with the Fab-folate conjugate, while failing to recognize the unconjugated Fab fragment, thus confirming the success of the conjugation.

The ability of the Fab-folate conjugate to recognize the folate receptor was evaluated in a competition binding assay using $^3$H-labeled folate and KB cells, a folate receptor-positive human nasopharyngeal carcinoma cell line. This showed that binding of the labeled folate to KB cells was inhibited by the Fab-folate conjugate and by a conjugate of folate with the intact 1D6.14 antibody, but not by the antibody alone. Thus, the conjugation of folate to the Fab fragment of the neutralizing antibody had not destroyed the ability of folate to bind to its receptor.

Whether the conjugation of folate to the neutralizing anti-knob Fab fragment had affected its ability to block adenovirus infection was then determined. AdCMVLuc, an E1-, E3-deleted Ad5 vector which expresses firefly luciferase from the cytomegalovirus (CMV) promoter, was premixed with various concentrations of the Fab-folate conjugate prior to infection of HeLa cell monolayers. Expression of luciferase activity in infected cells was determined 24 hours post-infection: this value is directly proportional to the number of infecting virus particles. The Fab-folate conjugate was confirmed as being capable of neutralizing adenoviral infection. This neutralization was dose-dependent, with maximal inhibition occurring with 0.5 mg Fab-folate.

Figure 17:
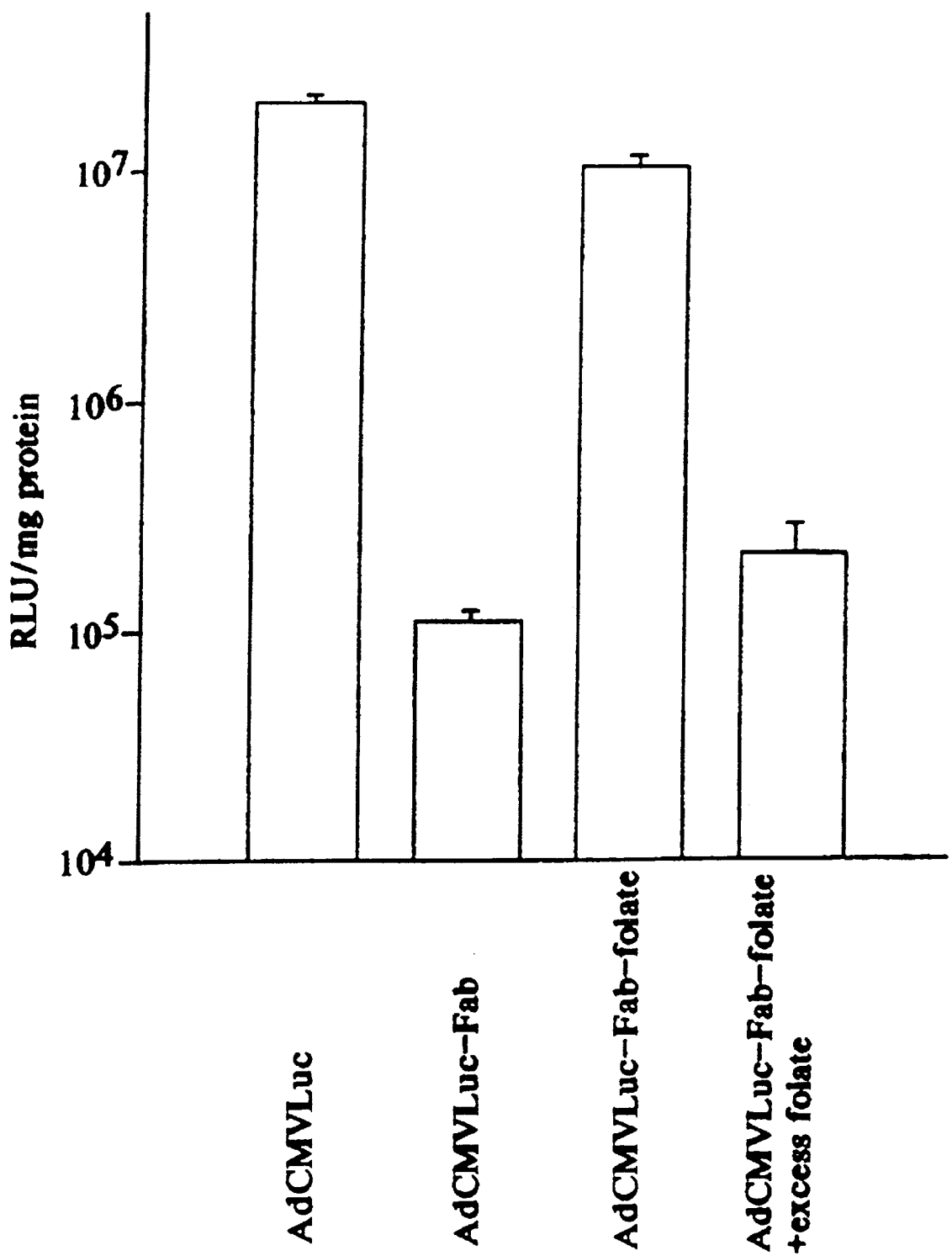
FIG. 17 shows the redirection of adenoviral infection mediated by the conjugate of folate with the Fab fragment of neutralizing mAb 1D6.14. Carboxyl groups of folate were coupled to amine groups of the Fab fragment of mAb 1D6.14 by a carbodiimide procedure, as described by Kranz, et al., *Proc. Nat. Acad. Sci. USA* 92, 9057–9061 (1995). Immunoblot analysis employing mouse anti-folic acid ascites fluid (Sigma) revelaled the success of the conjugation. The ability of the Fab-folate conjugate to recognize the folate receptor was confirmed in a competition binding assay conducted in triplicate using [$^3$H]-folate (Amersham; specific activity=47 Ci/mmol) and KB cells rinsed well with PBS to remove excess folate present in the culture medium. Next, the amount of 1D6.14 Fab or Fab-folate (0.5 mg) which gave maximum inhibition of infection by $10^8$ particles of AdCMVLuc was determined. This optimal dose of Fab or Fab-folate was then incubated with $10^8$ particles of AdCMVLuc at room temperature in a total volume of 20 ml HBS. After 30 minutes, the complexes were diluted to 1 ml with folate-free RPMI 1640 (ffRPMI; Gibco-BRL)+2% FCS and added in triplicate to 6-well plates containing 80% confluent KB cells which had been washed with PBS. Prior to infection, the target cells had been passaged twice in ffRPMI. After incubation for 24 hours at 37° C., the cells were lysed and extracts assayed for luciferase activity as described. For folate inhibition studies, KB cells were preincubated for 30 minutes at room temperature in 3 ml ffRPMI+10% FCS containing 50 mg folate, and the AdCMVLuc-Fab-folate complex was added to the cells in 1 ml ffRPMI+2% FCS containing 50 mg folate. Results are the mean of triplicate experiments.
Figure 18:
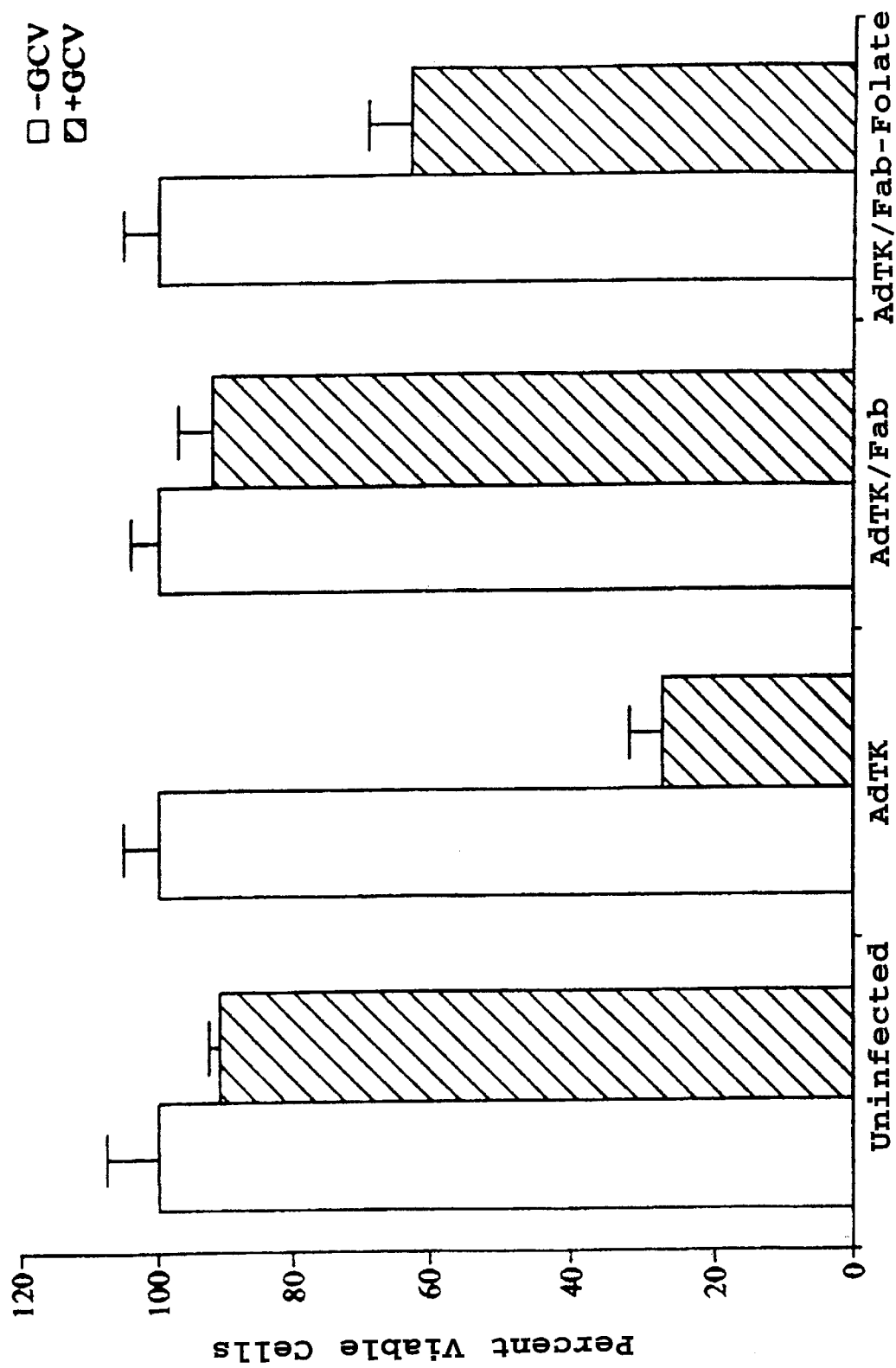
FIG. 18 shows the targeted killing of cells by an adenoviral vector redirected via the folate receptor. KB cells were plated in 96 well plates at 10,000 cells per well. The following day, cells were either left uninfected or treated at an moi of 10 with AdCMVHSV-TK alone or complexed with the previously determined optimal neutralizing amount of 1D6.14 Fab, Fab or Fab-folate as described for FIG. 21 (n=8). Half of the samples were treated 24 hours post-infection with ffRPMI+10% FCS containing the prodrug GCV at a concentration of 20 mM; the remaining cells were given only ffRPMI+10% FCS. Cell viability was determined 6 days later using a colorimetric cell proliferation assay that measured the conversion of a tetrazolium salt to formazan by viable cells as described by the manufacturer (Cell Titer 96 Aqueous Non-radioactive MTS Cell Proliferation Assay; Promega). Briefly, 20 ml of assay mixture were added to each well of cells and the plates incubated for 1–4 hrs at 37° C. before absorbance was measured at 490 nm in a 96 well plate reader (Molecular Devices). In these experiments KB cells were plated on the day of the assay in ffRPMI to generate a standard curve. Cells were removed by trypsinization and plated in triplicate wells at the following densities: 50,000; 20,000; 10,000; 5,000; 2,000; and 0 cells per well. From the standard curve, viable cell numbers could be calculated for experimental groups using the SOFTmax computer software (Molecular Devices).

Having verified the reagents, that the Fab-folate conjugate was capable of modifying the tropism of an adenoviral vector to permit specific targeting of the folate receptor was demonstrated. The adenoviral vector AdCMVLuc was premixed with the optimal neutralizing concentrations of the unconjugated Fab fragment or the Fab-folate conjugate prior to infection of KB cell monolayers maintained in folate-free medium. The level of luciferase activity was determined 24 hours post-infection. As shown in FIG. 17, AdCMVLuc was able to infect KB cells at a level such that greater than $10^7$ relative light units were expressed per microgram of cellular protein. In contrast, the unconjugated Fab fragment blocked infection of KB cells by AdCMVLuc by preventing the knob domain of the virus fiber from binding to its cellular receptor, thus resulting in a 99% decrement of luciferase expression. However, a high level of luciferase activity was restored when AdCMVLuc was premixed with the Fab-folate conjugate, indicating that the retargeted virus was capable of efficient infection. When a competition experiment was performed in which the target cells were preincubated in folate-containing medium and the infection carried out in the presence of excess free folate, the Fab-folate conjugate failed to mediate infection of KB cells by AdCMVLuc: the free folate saturated the target receptor, preventing the binding of the viral complex. Thus, the Fab-folate conjugate redirected adenoviral infection of target cells specifically via the folate receptor.

To demonstrate the ability of the Fab-folate conjugate to redirect toxin-mediated cell killing, an E1-deleted Ad5 vector which expresses the prodrug-activating herpes simplex virus thymidine kinase (HSV-TK) gene from the CMV promoter was utilized for infection of KB cells (18). Cells infected with AdCMVHSV-TK and subsequently treated with ganciclovir (GCV) demonstrated 73% cell death as expected. In contrast, when AdCMVHSV-TK was mixed with the neutralizing Fab only 8% of the KB cells were eradicated, indicating nearly 90% inhibition of TK/GCV mediated cell killing due to neutralization of adenoviral binding. Retargeting of the AdCMVHSV-TK vector with the Fab-folate conjugate restored TK/GCV mediated cell killing with eradication of almost 40% of the total cell population. This retargeting was specific for folate, as an excess of folate added to the AdCMVHSV-TK/Fab-folate infection media resulted in an inhibition of cell death comparable to that seen with the Fab alone. Thus, not only could TK/GCV mediated cell killing be ablated with the neutralizing Fab, but retargeting of the virus via Fab-folate successfully overcame this inhibition and resulted in specific tumor cell eradication.

The present invention shows that a vector derived from Ad5, which possessed chimeric fibers composed of the tail and shaft domains of Ad5 and the knob domain of Ad3, specifically targeted the Ad3 cellular receptor. This demonstrated that it is possible to alter the Ad5 receptor recognition profile and supports the idea that one can develop adenoviral vectors capable of targeted gene delivery to cells possessing specific surface receptor molecules. Furthermore, the present invention demonstrated that by complexing AdCMVLuc with Fab-folate, viral infection of target cells is specifically redirected via the folate receptor, resulting in a level of gene transfer comparable to that achieved by native adenoviral infection, which is in marked contrast to the inefficient infection exhibited by retargeted retroviral vectors. Furthermore, evidence of the utility of this targeting strategy for cancer gene therapy was provided by demonstrating that the Fab-folate conjugate can modify the tropism of AdCMVHSV-TK to achieve the killing of tumor cells expressing the folate receptor.

Since the adenoviral particles targeted to the folate receptor are too large to be accommodated within caveolae, the viruses could not have been internalized by potocytosis, the mechanism by which folate-macromolecule complexes enter cells. Therefore, that the Fab-folate conjugate redirected adenoviral infection specifically via the folate receptor indicates that modification of the first step of Ad infection, attachment of the knob domain of the fiber to primary cell surface receptors, does not affect the ability of the virus to accomplish the second step of infection, internalization. This is supported by the showing that binding-incompetent adenovirus facilitates molecular conjugate-mediated gene transfer by the receptor-mediated endocytosis pathway. In this case, it was shown that binding of the adenovirus to its native receptor is not a prerequisite for adenoviral-mediated endosome disruption: thus, the processes of adenoviral binding and subsequent entry steps are not functionally linked. This suggests that the range of cell-targeting ligands which can be employed in the construction of tropism-modified Ad vectors need not be restricted by the native internalization pathway of the ligand. The present invention provides strong evidence that a person having ordinary skill in this art can generate tropism-modified adenoviral vectors capable of targeted cell-specific gene delivery via a non-adenoviral receptor. Such a vector will enormously expand the potential therapeutic approaches which may be attempted employing gene therapy strategies.

The following references were cited herein:
1. Jolly, D., in *Cancer Gene Therapy*, eds. Appleton & Lange, pp. 51–64, (1994).
2. Trapnell, B. C., et al., *Current Opinion in Biotechnology* 5:617–625, (1994).
3. Siegfried., *Exp Clin Endocrinol* 101:7–11, (1993).
4. Bout, A., et al., *Human Gene Therapy* 5:3–10, (1994).
5. La Salle, G. L. G., et al., *Science* 259:988–990, (1993).
6. Csete, M. E., et al., *Transplantation Proceedings* 26(2):756–757, (1994).
7. Maeda, H., et al., *Gastroenterology* 106:1638–1644, (1994).
8. Jaffe, H. A., et al., *Nature Genetics* 1:372–378, (1992).
9. DeMatteo, R. P., et al., *Annals Of Surgery* 222(3):229–242, (1995).
10. Mastrangeli, A., et al., *Am J Physiol* 266:G1146–G1155, (1994).
11. Moullier, P., et al., *Kidney International* 45:1220–1225, (1994).
12. Mitani, K., et al., *Human Gene Therapy* 5:941–948, (1994).
13. Crystal, R. G., et al., *Nature Genetics* 8:42–51, (1994).
14. Clayman, G. L., et al., *Cancer Gene Therapy* 2(2):105–11, (1995).
15. Liu, T.-J., et al., *Cancer Research* 54:3662–3667, (1994).
16. Smythe, W. R., et al., *Ann Thorac Surg* 57:1395–1401, (1994).
17. Fujiwara, T., et al., *Cancer Research* 54:2287–2291, (1994).
18. Addison, C. L., et al., *Proc Natl Acad Sci* 92:8522–8526, (1995).
19. Strattford-Perricaudet, L., et al., *J Clin Invest* 90:626–630, (1992).
20. Huard, J., et al., *Gene Therapy* 2:107–115, (1995).
21. Henry, L. J., et al., *Journal of Virology* 68:5239–5246, (1994).
22. Stevenson, S. C., et al., *J. of Virology* 69:2850–2857, (1995).
23. Louis, N., et al., *Journal of Virology* 68:4104–4106, (1994).
24. Michael, S. I., et al., *Gene Therapy*, 2:660–669, (1995).
25. Mittal, S. K., et al., *Virus Research* 28:67–90, (1993).
26. McGrory, W. J., et al., *Virology* 163:614–617, (1988).
27. Graham, F. L., et al., *J Gen Virol* 36:59–72, (1977).
28. Graham, F. L., et al., *Methods in Molec. Biology* 7:109–128, (1991).
29. Davidson, D., et al., *Journal of Virology* 61:1226–1239, (1987).
30. Ballay, A., et al., *The EMBO Journal* 4:3861–3865, (1985).
31. Berkner, K. L., et al., *Journal of Virology* 61:1213–1220, (1987).
32. Boudin, M.-L., et al., *Virology* 116:589–604, (1982).
33. Falgout, B., et al., *Journal of Virology* 62:622–625, (1988).
34. Douglas, J. T., et al., *Tumor Targeting* 1:67–84, (1995).
35. Yee, J.-K., et al., *Methods in Cell Biology* 43:99–112, (1994).
36. Kasahara, N., et al., *Science* 266:1373–1376, (1994).
37. Cardoso, J. E., et al., *Human Gene Therapy* 4:411–418, (1993).
38. Plaat, D., et al., *Virology* 98:55–62, (1979).
39. Defer, C., et al., *Journal of Virology* 64:3661–3673, (1990).
40. Bai M., et al., *J. Virol.* 67:5198–5205, (1993).
41. Bett A., et al., *Proc. Natl. Acad. Sci. USA* 91:8802–8806, (1994).
42. Chroboczek J., et al., Adenovirus fiber, p. 163–200. In The molecular repertoire of adenoviruses I, W. Doerfler and P. Bohm (ed.), Springer-Verlag. Berlin/New York, (1995).
43. Chu T.-H., et al., *J. Virol.* 69:2659–2663, (1995).
44. Chu T.-H., et al., *Gene Ther.* 1:292–299, (1994).
45. Clayman G., et al., *Cancer Res.* 55:1–6, (1995).
46. Cosset F.-L., et al., *J. Virol.* 69:6314–6322, (1995).
47. Dong J., et al., *J. Virol.* 66:7374–7382, (1992).
48. Emi N., et al., *J. Virol.* 65:1202–1207, (1991).
49. Ghosh-Choudhury G., et al., *EMBO J.* 6:1733–1739, (1987).
50. Greber U., et al., *Cell* 1993:477–486, (1993).
51. Han X., et al., *Proc. Natl. Acad. Sci. USA* 92:9747–9751, (1995).
52. Mathias P., et al., *J. Virol.* 68:6811–6814, (1994).
53. Michael S., et al., *J. Biol. Chem.* 268:6866–6869, (1993).
54. Novelli A., et al., *J. Biol. Chem.* 266:9299–9303, (1991a).
55. Novelli A., et al., *Virology* 185:365–376, (1991b).
56. Philipson L., et al., *J. Virol.* 2:1064–1075, (1968).
57. Russell S., et al., *Nucleic Acids Res.* 21:1081–1085, (1993).
58. Seth P., et al., Pathway of adenovirus entry into cells., p. 191–195. In R. Crowell and K. Lonberg-Holm (ed.), Virus attachment and entry into cells. American Society for Microbiology, Washington, D.C., (1986).
59. Somia N., et al., *Proc. Natl. Acad. Sci. USA* 92:7570–7574, (1995).
60. Takeuchi Y., et al., *J. Virol.* 68:8001–8007, (1994).
61. Valsesia-Wittmann S., et al., *J. Virol.* 68:4609–4619, (1994).
62. Weiss R., et al., *Virology* 76:808–825, (1977).
63. Wickham T., et al., *Gene Ther.* 2:750–756, (1995).
64. Wickham T., et al., *J. Cell Biol.* 127:257–264, (1994).
65. Wickham T., et al., *Cell* 73:309–319, (1993).
66. Yee J.-K., et al., *Proc. Natl. Acad. Sci. USA* 91:9564–9568, (1994).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A targeted adenovirus lacking endogenous viral tropism but having a novel tropism, said targeted adenovirus comprising:

(1) a neutralizing anti-fiber antibody, or antibody fragment, or fusions thereof, linked to a cell specific attachment moiety to form a conjugate; and (2) an adenoviral vector containing a reporter gene, wherein said conjugate is complexed with said vector to form a targeted adenovirus redirected to infect target cells via the cell-specific ligand.

2. The targeted adenovirus of claim 1, wherein said cell specific attachment moiety is selected from the group consisting of physiological ligands, anti-receptor antibodies or cell specific peptides.

3. The targeted adenovirus of claim 1, wherein said adenoviral vector further contains a therapeutic gene.

4. The targeted adenovirus of claim 3, wherein said therapeutic gene is the herpes simplex virus-thymidine kinase gene.

5. A method of making a targeted adenoviral vector lacking endogenous viral tropism but having a novel tropism, comprising the steps of:

linking a neutralizing anti-fiber antibody, or antibody fragment, or fusions thereof, to a cell specific attachment moiety to form a conjugate; and complexing said conjugate with an adenoviral vector containing a reporter gene so as to form a recombinant adenoviral vector which can bind to a target cell via a non-adenoviral cellular receptor.

6. The method of claim 5, wherein said cell-specific ligand is selected from the group consisting of the physiological ligands, anti-receptor antibodies or cell specific peptides.

7. The method of claim 5, wherein said adenoviral vector further contains a therapeutic gene.

8. The method of claim 7, wherein said therapeutic gene is the herpes simplex virus-thymidine kinase gene.

9. A targeted adenovirus lacking endogenous viral tropism but having a novel tropism prepared by the method of claim 5.

10. A method of killing tumor cells in an individual in need of such treatment, comprising the steps of:

pretreating said individual with an effective amount of the adenoviral vector of claim 8; and administering ganciclovir to said individual.

\* \* \* \* \*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 12 basepairs
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no
    ( x i ) SEQUENCE DESCRIPTION:SEQ ID NO: 1:

CCCCAATTGG GG 12

( 2 ) INFORMATION FOR SEQ ID NO:2:

( i ) SEQUENCE CHARACTERISTICS:
        ( A ) LENGTH: 25 basepairs
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 2:

ATGAAGCGCG CCAGACCGTC TGAAG 25

( 2 ) INFORMATION FOR SEQ ID NO:3:

( i ) SEQUENCE CHARACTERISTICS:
        ( A ) LENGTH: 31 basepairs
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 3:

TTAGAGCTCT TGGGCAATGT ATGAAAAAGT G 31

( 2 ) INFORMATION FOR SEQ ID NO:4:

( i ) SEQUENCE CHARACTERISTICS:
    ( A ) LENGTH: 57 basepairs
    ( B ) TYPE: nucleic acid
    ( C ) STRANDEDNESS: single-stranded
    ( D ) TOPOLOGY: linear ( i i ) MOLECULE TYPE:
    ( A ) DESCRIPTION: other nucleic acid ( i i i ) HYPOTHETICAL: no ( i v ) ANTI-SENSE: no ( x i ) SEQUENCE DESCRIPTION:SEQ ID NO: 4:

```
CTCTAAAGAA  TCGTTTGTGT  TATGTTTCAA  CGTGTTTATT  TTTCAATTGA          50

AGCTTAT                                                             57
```

( 2 ) INFORMATION FOR SEQ ID NO:5:

( i ) SEQUENCE CHARACTERISTICS:
        ( A ) LENGTH: 59 basepairs
        ( B ) TYPE: nucleic acid
        ( C ) STRANDEDNESS: single-stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 5:

```
CGATAAGCTT  CAATTGAAAA  ATAAACACGT  TGAAACATAA  CACAAACGAT          50

TCTTTAGAG                                                           59
```

( 2 ) INFORMATION FOR SEQ ID NO:6:

( i ) SEQUENCE CHARACTERISTICS:
        ( A ) LENGTH: 25 basepairs
        ( B ) TYPE: nucleic acid
        ( C ) STRANDEDNESS: single-stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 6:

```
ATGCACCAAA  CACAAATCCC  CTCAA                                       25
```

( 2 ) INFORMATION FOR SEQ ID NO:7:

( i ) SEQUENCE CHARACTERISTICS:
        ( A ) LENGTH: 32 basepairs
        ( B ) TYPE: nucleic acid
        ( C ) STRANDEDNESS: single-stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 7:

CTCTTTCCCG GGTTAGCTTA TCATTATTTT TG                32

(2) INFORMATION FOR SEQ ID NO:8:

(i) SEQUENCE CHARACTERISTICS:
        (A) LENGTH: 25 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 8:

TATGGACAGG TCCAAAACCA GAAGC                25

(2) INFORMATION FOR SEQ ID NO:9:

(i) SEQUENCE CHARACTERISTICS:
        (A) LENGTH: 33 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 9:

TTTATTAGTC ATCTTCTCTA ATATAGGAAA AGG                33

(2) INFORMATION FOR SEQ ID NO:10:

(i) SEQUENCE CHARACTERISTICS:
        (A) LENGTH: 23 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 10:

AACAAAATGT GGCAGTCAAA TAC                23

(2) INFORMATION FOR SEQ ID NO:11:

(i) SEQUENCE CHARACTERISTICS:
        (A) LENGTH: 22 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 11:

CATACATTGC GCAAGAATAA AG                                                                                   22

(2) INFORMATION FOR SEQ ID NO:12:

(i) SEQUENCE CHARACTERISTICS:
        (A) LENGTH: 22 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 12:

CTTTATTCTT GCGCAATGTA TG                                                                                   22

(2) INFORMATION FOR SEQ ID NO:13:

(i) SEQUENCE CHARACTERISTICS:
        (A) LENGTH: 23 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 13:

TGATGCACGA TTATGACTCT ACC                                                                                  23

(2) INFORMATION FOR SEQ ID NO:14:

(i) SEQUENCE CHARACTERISTICS:
        (A) LENGTH: 31 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 14:

TTTAAGGATT CCGGTGCCAT TACAGTAGGA A                                                                         31

(2) INFORMATION FOR SEQ ID NO:15:

(i) SEQUENCE CHARACTERISTICS:
        (A) LENGTH: 30 basepairs
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (xi) SEQUENCE DESCRIPTION:SEQ ID NO: 15:

```
TATATAAGCT   TATTCTTGGG   CAATGTATGA                                                    30
```

( 2 ) INFORMATION FOR SEQ ID NO:16:

( i ) SEQUENCE CHARACTERISTICS:
        ( A ) LENGTH: 33 basepairs
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 16:

```
CTCGGATCCA   ATTCTATTGC   ACTGAAAAAT   AAC                                              33
```

( 2 ) INFORMATION FOR SEQ ID NO:17:

( i ) SEQUENCE CHARACTERISTICS:
        ( A ) LENGTH: 36 basepairs
        ( B ) TYPE: nucleic acid
        ( C ) STRANDEDNESS: single- stranded
        ( D ) TOPOLOGY: linear ( i i ) MOLECULE TYPE:
        ( A ) DESCRIPTION: other nucleic acid ( i i i ) HYPOTHETICAL: no ( i v ) ANTI-SENSE: no ( x i ) SEQUENCE DESCRIPTION:SEQ ID NO: 17:

```
GGGAAGCTTA   GTCATCTTCT   CTAATATAGG   AAAAGG                                           36
```